United States Patent
O'Hehir et al.

(10) Patent No.: US 9,120,865 B2
(45) Date of Patent: Sep. 1, 2015

(54) T CELL EPITOPES OF THE CYN D 1 ALLERGEN FROM BERMUDA GRASS POLLEN

(75) Inventors: Robyn O'Hehir, Parkville (AU); Jennifer Rolland, Melbourne (AU)

(73) Assignee: Circassia Limited, Oxford (GB)

( * ) Notice: Subject to any disclaimer, the term of this patent is extended or adjusted under 35 U.S.C. 154(b) by 0 days.

(21) Appl. No.: 12/871,575

(22) Filed: Aug. 30, 2010

(65) Prior Publication Data

US 2011/0217325 A1 Sep. 8, 2011

Related U.S. Application Data

(63) Continuation of application No. 10/489,972, filed as application No. PCT/AU02/01283 on Sep. 18, 2002, now abandoned.

(30) Foreign Application Priority Data

Sep. 18, 2001 (AU) ................................ 2001007754

(51) Int. Cl.

| | |
|---|---|
| A61K 38/00 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |
| C07K 17/00 | (2006.01) |
| A61K 39/00 | (2006.01) |
| A61K 39/35 | (2006.01) |
| A61K 38/04 | (2006.01) |
| C07K 14/415 | (2006.01) |
| A61K 39/36 | (2006.01) |
| C07K 16/16 | (2006.01) |

(52) U.S. Cl.
CPC .............. *C07K 14/415* (2013.01); *A61K 39/36* (2013.01); *A61K 38/00* (2013.01); *A61K 39/35* (2013.01); *C07K 7/00* (2013.01); *C07K 16/16* (2013.01)

(58) Field of Classification Search
CPC ........ C07K 7/00; C07K 14/415; C07K 16/16; A61K 39/36; A61K 38/00; A61K 39/35
See application file for complete search history.

(56) References Cited

U.S. PATENT DOCUMENTS 5,480,972 A 1/1996 Avjioglu et al.
6,214,358 B1 4/2001 Singh et al.

FOREIGN PATENT DOCUMENTS

| WO | 89/09260 A1 | 10/1989 |
|---|---|---|
| WO | 92/16554 A1 | 10/1992 |
| WO | WO 93/10236 | * 5/1993 |

OTHER PUBLICATIONS

Greenspan et al. (Nature Biotechnology 17: 936-937, 1999).*
Bowie et al. (Science, 1990, 257:1306-1310).*
Smith et al., J. Allergy Clin. Immunol, 1996; 331-343.*
Patronov et al., Open Biol., 2013; 3: 1-13.*
Blaher, Bella et al., "Identification of T-cell epitopes of Lol p 9, a major allergen of ryegrass (*Lolium perenne*) pollen," J. Allergy Clin. Immunol., vol. 98:124-132 (1996).
Boslego, John W. et al., "Gonorrhea Vaccines," Vaccines, Chpt. 17, Stanley A. Plotkin (Ed.), W.B. Saunders Company, pp. 211-223 (1988).
Chang, Z.N. et al., "Analysis of allergenic components of Bermuda grass pollen by monoclonal antibodies," Allergy, vol. 46:520-528 (1991).
Chang, Zo-Nan et al., "Using Monoclonal Antibodies to Characterize a Sequential Epitope on the Group I Allergen of Bermuda Grass Pollen," Int. Arch. Allergy Immunol., vol. 114:258-264 (1997).
De Lalla, Claudia et al., "Cutting Edge: Identification of Novel T Cell Epitopes in Lol p5a by Computational Prediction," The Journal of Immunology, vol. 163:1725-1729 (1999).
Ellis, Ronald W., "New Technologies for Making Vaccines," New Vaccine Technologies, Landes Bioscience, Medical Intelligence Unit 26, chpt. 29, pp. 568-575 (1998).
Eusebius, Nirupama et al., "Oligoclonal Analysis of the Atopic T Cell Response to the Group 1 Allergen of *Cynodon dactylon* (Bermuda Grass) Pollen: Pre- and Post-Allergen-Specific Immunotherapy," Int. Arch. Allergy Immunol., vol. 127:234-244 (2002).
Ford, S.A. et al., "Identification of Bermuda grass (*Cynodon dactylon*)—pollen allergens by electroblotting," J. Allergy Clin. Immunol., vol. 1987:711-720 (1987).
Han, Shou-Hwa et al., "Identification and characterization of epitopes on Cyn d I, the major allergen of Bermuda grass pollen," J. Allergy Clin. Immunol., vol. 91:1035-1041 (1993).

(Continued)

*Primary Examiner* — Gary Nickol
*Assistant Examiner* — Lakia Tongue
(74) *Attorney, Agent, or Firm* — Nelson Mullins Riley & Scarborough LLP; Jane E. Remillard, Esq.; Jeanne M. DiGiorgio

(57) ABSTRACT

The present invention relates generally to molecules such as peptides, polypeptides and proteins which interact immunologically with T lymphocytes in subjects having Bermuda grass allergy and genetic sequences encoding same. These molecules are preferentially immunointeractive with T cells in subjects having a Bermuda grass pollen allergy. The molecules of the present invention are useful in the development of diagnostic, therapeutic and prophylactic agents for conditions characterized by an aberrant, inappropriate or otherwise unwanted immune response to Bermuda grass pollen or derivative or homolog thereof.

17 Claims, 6 Drawing Sheets

(56) References Cited

OTHER PUBLICATIONS

Figure 1:
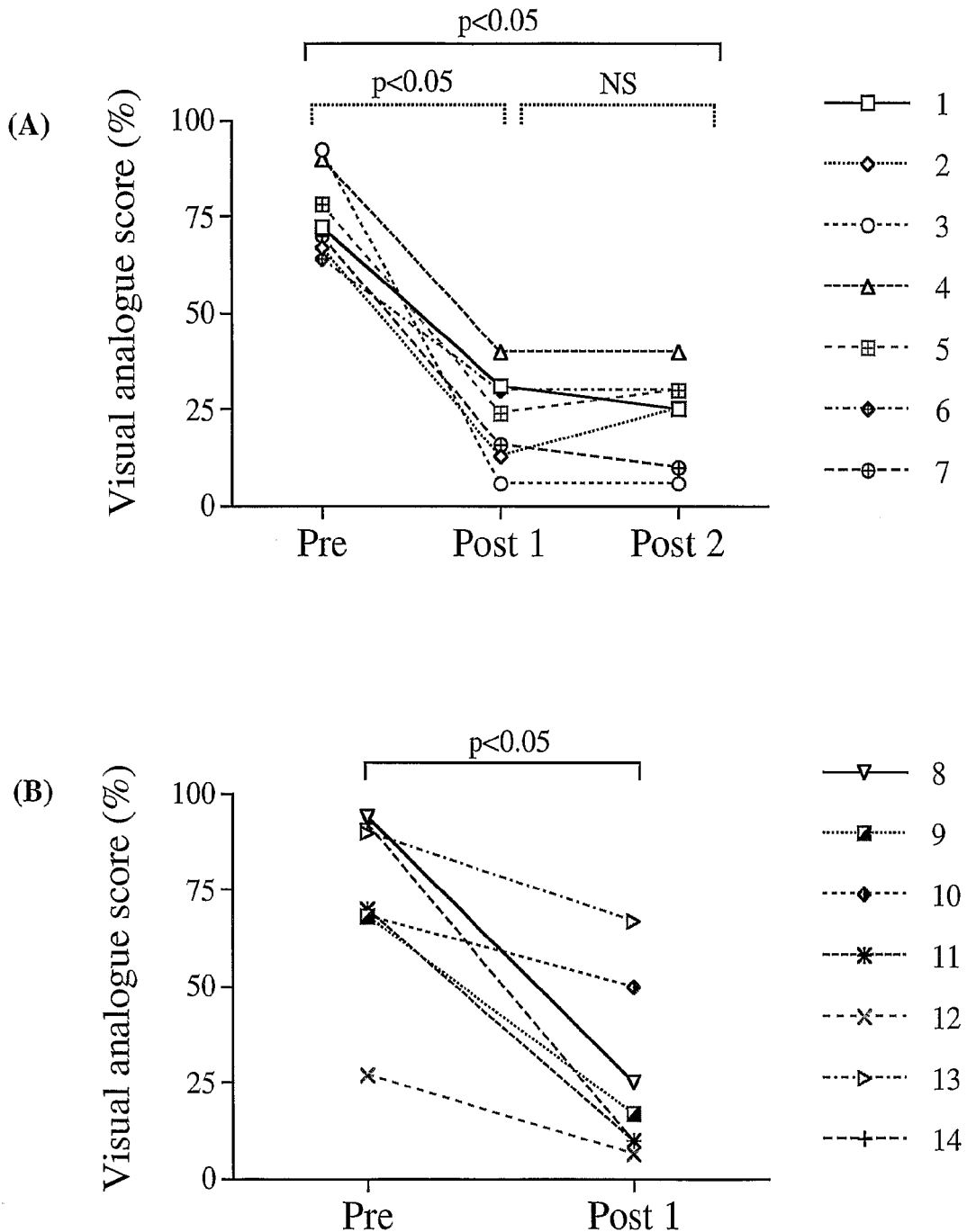

Matthiesen, F. et al., "Characteristics of grass pollen allergens," Epitopes of Atopic Allergens, Proceedings of Workshop held under the Aegis of the XIVth Congress of the European Academy of Allergy and Clinical Immunology, Berlin, pp. 9-13 (1989).

Matthiesen, F. et al., "Characterization of the Major Allergen of *Cynodon dactylon* (Bermuda Grass) Pollen," The Journal of Allergy and Clinical Immunology, vol. 81:266, No. 393 (1988).

Matthiesen, Finn et al., "Characterization of the major allergen of *Cynodon dactylon* (Bermuda Grass) pollen, Cyn d I," J. Allergy Clin. Immunol., vol. 88:763-774 (1991).

Matthiesen, F. et al., "Monoclonal Antibodies Against Group I and Group V Allergens of Grass Pollens," Clinical and Experimental Allergy, Abstracts of the EAACI 1990 Meeting, p. 47, No. OP48 (1990).

Orren, Ann et al., "Studies on Bermuda Grass Pollen Allergens," SA Medical Journal, vol. 51(17):586-591 (1977).

Perez, Mary et al., "cDNA Cloning and Immunological Characterization of the Rye Grass Allergen Lol p I," The Journal of Biological Chemistry, vol. 265(27):16210-16215 (1990).

Schenk, Siegfried et al., "T Cell Epitopes of Phl p 1, Major Pollen Allergen of Timothy Grass (*Phleum pratense*), Crossreactivity with Group I Allergens of Different Grasses," Advances in Experimental Medicine and Biology, vol. 409:141-146 (1996).

Schenk, Siegfried et al., "T Cell Epitopes of Phl p. 1, Major Pollen Allergen of Timothy Grass (*Phleum pratense*): Evidence for Crossreacting and Non-crossreacting T-cell Epitopes within Grass Group I Allergens," J. Allergy Clin. Immunol., vol. 96(1):986-996 (1995).

Shen, Horng-Der et al., "Identification of allergens and antigens of Bermuda grass (*Cynodon dactylon*) pollen by immunoblot analysis," Clinical Allergy, vol. 18:401-409 (1988).

Singh, Mohan B. et al., "Molecular Biology of Rye-Grass Pollen Allergens," Baldo BA (ed.): Molecular Approaches to the Study of Allergens. Monogr. Allergy. Basel, Karger, vol. 28:101-120 (1990).

Suphioglu, Cenk et al., "Peptide Mapping Analysis of Group I Allergens of Grass Pollens," Int. Arch. Allergy Immunol., vol. 102:144-151 (1993).

Suphioglu, Cenk et al., "Recombinant Expression and Epitope Mapping of Grass Pollen Allergens," Advances in Experimental Medicine and Biology, vol. 409:147-155 (1996).

\* cited by examiner (SEQ ID NO:2) (1-20)    AIGDKPGPNITATYGNKWLE
(SEQ ID NO:3) (10-29)           ITATYGNKWLEAKATFYGSN
(SEQ ID NO:4) (19-38)                    LEAKATFYGSNPRGAAPDDH
(SEQ ID NO:5) (28-47)                            SNPRGAAPDDHGGACGYKDV (SEQ ID NO:6) (37-56)   DHGGACGYKDVDKPPFDGMT
(SEQ ID NO:7) (46-65)           DVDKPPFDGMTACGNEPIFK
(SEQ ID NO:8) (55-74)                    MTACGNEPIFKDGLGCGACY
(SEQ ID NO:9) (64-83)                            FKDGLGCGACYEIKCKEPVE (SEQ ID NO:10) (73-92)  CYEIKCKEPVECSGEPVLVK
(SEQ ID NO:11) (82-101)         VECSGEPVLVKITDKNYEHI
(SEQ ID NO:12) (91-110)                  VKITDKNYEHIAAYHFDLSG
(SEQ ID NO:13) (100-119)                         HIAAYHFDLSGKAFGAMAKK (SEQ ID NO:14) (109-128)SGKAFGAMAKKGQEDKLRKA
(SEQ ID NO:15) (118-137)        KKGQEDKLRKAGELTLQFRR
(SEQ ID NO:16) (127-146)                 KAGELTLQFRRVKCKYPSGT
(SEQ ID NO:17) (136-155)                         RRVKCKYPSGTKITFHIEK( (SEQ ID NO:18) (145-164)GTKITFHIEKGSNDHYLALL
(SEQ ID NO:19) (154-173)        KGSNDHYLALLVKYAAGDGN
(SEQ ID NO:20) (163-182)                 LLVKYAAGDGNIVAVDIKPK
(SEQ ID NO:21) (172-191)                         GNIVAVDIKPKDSDEFIPMK (SEQ ID NO:22) (181-200)PKDSDEFIPMKSSWGAIWRI
(SEQ ID NO:23) (190-209)        MKSSWGAIWRIDPKKPLKGP
(SEQ ID NO:24) (199-218)                 RIDPKKPLKGPFSIRLTSEG
(SEQ ID NO:25) (208-227)                         GPFSIRLTSEGGAHLVQDD\

(SEQ ID NO:26) (217-236)EGGAHLVQDDVIPANWKPDT
(SEQ ID NO:27) (222-241)     LVQDDVIPANWKPDTVYTSK
(SEQ ID NO:28) (227-246)          VIPANWKPDTVYTSKLQFGA

Figure 2

SEQUENCE LISTING

```
<160> NUMBER OF SEQ ID NOS: 28

<210> SEQ ID NO 1
<211> LENGTH: 246
<212> TYPE: PRT
<213> ORGANISM: human

<400> SEQUENCE: 1

Ala Ile Gly Asp Lys Pro Gly Pro Asn Ile Thr Ala Thr Tyr Gly Asn
1               5                   10                  15
```

```
Lys Trp Leu Glu Ala Lys Ala Thr Phe Tyr Gly Ser Asn Pro Arg Gly
            20                  25                  30

Ala Ala Pro Asp Asp His Gly Gly Ala Cys Gly Tyr Lys Asp Val Asp
        35                  40                  45

Lys Pro Pro Phe Asp Gly Met Thr Ala Cys Gly Asn Glu Pro Ile Phe
    50                  55                  60

Lys Asp Gly Leu Gly Cys Gly Ala Cys Tyr Glu Ile Lys Cys Lys Glu
65                  70                  75                  80

Pro Val Glu Cys Ser Gly Glu Pro Val Leu Val Lys Ile Thr Asp Lys
                85                  90                  95

Asn Tyr Glu His Ile Ala Ala Tyr His Phe Asp Leu Ser Gly Lys Ala
            100                 105                 110

Phe Gly Ala Met Ala Lys Lys Gly Gln Glu Asp Lys Leu Arg Lys Ala
        115                 120                 125

Gly Glu Leu Thr Leu Gln Phe Arg Arg Val Lys Cys Lys Tyr Pro Ser
    130                 135                 140

Gly Thr Lys Ile Thr Phe His Ile Glu Lys Gly Ser Asn Asp His Tyr
145                 150                 155                 160

Leu Ala Leu Leu Val Lys Tyr Ala Ala Gly Asp Gly Asn Ile Val Ala
                165                 170                 175

Val Asp Ile Lys Pro Lys Asp Ser Asp Glu Phe Ile Pro Met Lys Ser
            180                 185                 190

Ser Trp Gly Ala Ile Trp Arg Ile Asp Pro Lys Pro Leu Lys Gly
        195                 200                 205

Pro Phe Ser Ile Arg Leu Thr Ser Glu Gly Gly Ala His Leu Val Gln
    210                 215                 220

Asp Asp Val Ile Pro Ala Asn Trp Lys Pro Asp Thr Val Tyr Thr Ser
225                 230                 235                 240

Lys Leu Gln Phe Gly Ala
                245

<210> SEQ ID NO 2
<211> LENGTH: 20
<212> TYPE: PRT
<213> ORGANISM: human

<400> SEQUENCE: 2

Ala Ile Gly Asp Lys Pro Gly Pro Asn Ile Thr Ala Thr Tyr Gly Asn
1               5                   10                  15

Lys Trp Leu Glu
            20

<210> SEQ ID NO 3
<211> LENGTH: 20
<212> TYPE: PRT
<213> ORGANISM: human

<400> SEQUENCE: 3

Ile Thr Ala Thr Tyr Gly Asn Lys Trp Leu Glu Ala Lys Ala Thr Phe
1               5                   10                  15

Tyr Gly Ser Asn
            20

<210> SEQ ID NO 4
<211> LENGTH: 20
<212> TYPE: PRT
<213> ORGANISM: human
```

-continued

```
<400> SEQUENCE: 4

Leu Glu Ala Lys Ala Thr Phe Tyr Gly Ser Asn Pro Arg Gly Ala Ala
1               5                   10                  15

Pro Asp Asp His
            20

<210> SEQ ID NO 5
<211> LENGTH: 20
<212> TYPE: PRT
<213> ORGANISM: human

<400> SEQUENCE: 5

Ser Asn Pro Arg Gly Ala Ala Pro Asp Asp His Gly Gly Ala Cys Gly
1               5                   10                  15

Tyr Lys Asp Val
            20

<210> SEQ ID NO 6
<211> LENGTH: 20
<212> TYPE: PRT
<213> ORGANISM: human

<400> SEQUENCE: 6

Asp His Gly Gly Ala Cys Gly Tyr Lys Asp Val Asp Lys Pro Pro Phe
1               5                   10                  15

Asp Gly Met Thr
            20

<210> SEQ ID NO 7
<211> LENGTH: 20
<212> TYPE: PRT
<213> ORGANISM: human

<400> SEQUENCE: 7

Asp Val Asp Lys Pro Pro Phe Asp Gly Met Thr Ala Cys Gly Asn Glu
1               5                   10                  15

Pro Ile Phe Lys
            20

<210> SEQ ID NO 8
<211> LENGTH: 20
<212> TYPE: PRT
<213> ORGANISM: human

<400> SEQUENCE: 8

Met Thr Ala Cys Gly Asn Glu Pro Ile Phe Lys Asp Gly Leu Gly Cys
1               5                   10                  15

Gly Ala Cys Tyr
            20

<210> SEQ ID NO 9
<211> LENGTH: 20
<212> TYPE: PRT
<213> ORGANISM: human

<400> SEQUENCE: 9

Phe Lys Asp Gly Leu Gly Cys Gly Ala Cys Tyr Glu Ile Lys Cys Lys
1               5                   10                  15

Glu Pro Val Glu
            20
```

<210> SEQ ID NO 10
<211> LENGTH: 20
<212> TYPE: PRT
<213> ORGANISM: human

<400> SEQUENCE: 10

Cys Tyr Glu Ile Lys Cys Lys Glu Pro Val Glu Cys Ser Gly Glu Pro
1               5                   10                  15

Val Leu Val Lys
            20

<210> SEQ ID NO 11
<211> LENGTH: 20
<212> TYPE: PRT
<213> ORGANISM: human

<400> SEQUENCE: 11

Val Glu Cys Ser Gly Glu Pro Val Leu Val Lys Ile Thr Asp Lys Asn
1               5                   10                  15

Tyr Glu His Ile
            20

<210> SEQ ID NO 12
<211> LENGTH: 20
<212> TYPE: PRT
<213> ORGANISM: human

<400> SEQUENCE: 12

Val Lys Ile Thr Asp Lys Asn Tyr Glu His Ile Ala Ala Tyr His Phe
1               5                   10                  15

Asp Leu Ser Gly
            20

<210> SEQ ID NO 13
<211> LENGTH: 20
<212> TYPE: PRT
<213> ORGANISM: human

<400> SEQUENCE: 13

His Ile Ala Ala Tyr His Phe Asp Leu Ser Gly Lys Ala Phe Gly Ala
1               5                   10                  15

Met Ala Lys Lys
            20

<210> SEQ ID NO 14
<211> LENGTH: 20
<212> TYPE: PRT
<213> ORGANISM: human

<400> SEQUENCE: 14

Ser Gly Lys Ala Phe Gly Ala Met Ala Lys Lys Gly Gln Glu Asp Lys
1               5                   10                  15

Leu Arg Lys Ala
            20

<210> SEQ ID NO 15
<211> LENGTH: 20
<212> TYPE: PRT
<213> ORGANISM: human

<400> SEQUENCE: 15

Lys Lys Gly Gln Glu Asp Lys Leu Arg Lys Ala Gly Glu Leu Thr Leu

```
1               5                   10                  15

Gln Phe Arg Arg
            20

<210> SEQ ID NO 16
<211> LENGTH: 20
<212> TYPE: PRT
<213> ORGANISM: human

<400> SEQUENCE: 16

Lys Ala Gly Glu Leu Thr Leu Gln Phe Arg Arg Val Lys Cys Lys Tyr
1               5                   10                  15

Pro Ser Gly Thr
            20

<210> SEQ ID NO 17
<211> LENGTH: 20
<212> TYPE: PRT
<213> ORGANISM: human

<400> SEQUENCE: 17

Arg Arg Val Lys Cys Lys Tyr Pro Ser Gly Thr Lys Ile Thr Phe His
1               5                   10                  15

Ile Glu Lys Gly
            20

<210> SEQ ID NO 18
<211> LENGTH: 20
<212> TYPE: PRT
<213> ORGANISM: human

<400> SEQUENCE: 18

Gly Thr Lys Ile Thr Phe His Ile Glu Lys Gly Ser Asn Asp His Tyr
1               5                   10                  15

Leu Ala Leu Leu
            20

<210> SEQ ID NO 19
<211> LENGTH: 20
<212> TYPE: PRT
<213> ORGANISM: human

<400> SEQUENCE: 19

Lys Gly Ser Asn Asp His Tyr Leu Ala Leu Leu Val Lys Tyr Ala Ala
1               5                   10                  15

Gly Asp Gly Asn
            20

<210> SEQ ID NO 20
<211> LENGTH: 20
<212> TYPE: PRT
<213> ORGANISM: human

<400> SEQUENCE: 20

Leu Leu Val Lys Tyr Ala Ala Gly Asp Gly Asn Ile Val Ala Val Asp
1               5                   10                  15

Ile Lys Pro Lys
            20

<210> SEQ ID NO 21
<211> LENGTH: 20
<212> TYPE: PRT
```

<213> ORGANISM: human

<400> SEQUENCE: 21

Gly Asn Ile Val Ala Val Asp Ile Lys Pro Lys Asp Ser Asp Glu Phe
1               5                   10                  15

Ile Pro Met Lys
            20

<210> SEQ ID NO 22
<211> LENGTH: 20
<212> TYPE: PRT
<213> ORGANISM: human

<400> SEQUENCE: 22

Pro Lys Asp Ser Asp Glu Phe Ile Pro Met Lys Ser Ser Trp Gly Ala
1               5                   10                  15

Ile Trp Arg Ile
            20

<210> SEQ ID NO 23
<211> LENGTH: 20
<212> TYPE: PRT
<213> ORGANISM: human

<400> SEQUENCE: 23

Met Lys Ser Ser Trp Gly Ala Ile Trp Arg Ile Asp Pro Lys Lys Pro
1               5                   10                  15

Leu Lys Gly Pro
            20

<210> SEQ ID NO 24
<211> LENGTH: 20
<212> TYPE: PRT
<213> ORGANISM: human

<400> SEQUENCE: 24

Arg Ile Asp Pro Lys Lys Pro Leu Lys Gly Pro Phe Ser Ile Arg Leu
1               5                   10                  15

Thr Ser Glu Gly
            20

<210> SEQ ID NO 25
<211> LENGTH: 20
<212> TYPE: PRT
<213> ORGANISM: human

<400> SEQUENCE: 25

Gly Pro Phe Ser Ile Arg Leu Thr Ser Glu Gly Gly Ala His Leu Val
1               5                   10                  15

Gln Asp Asp Val
            20

<210> SEQ ID NO 26
<211> LENGTH: 20
<212> TYPE: PRT
<213> ORGANISM: human

<400> SEQUENCE: 26

Glu Gly Gly Ala His Leu Val Gln Asp Asp Val Ile Pro Ala Asn Trp
1               5                   10                  15

Lys Pro Asp Thr
            20

```
<210> SEQ ID NO 27
<211> LENGTH: 20
<212> TYPE: PRT
<213> ORGANISM: human

<400> SEQUENCE: 27

Leu Val Gln Asp Asp Val Ile Pro Ala Asn Trp Lys Pro Asp Thr Val
1               5                   10                  15

Tyr Thr Ser Lys
            20

<210> SEQ ID NO 28
<211> LENGTH: 20
<212> TYPE: PRT
<213> ORGANISM: human

<400> SEQUENCE: 28

Val Ile Pro Ala Asn Trp Lys Pro Asp Thr Val Tyr Thr Ser Lys Leu
1               5                   10                  15

Gln Phe Gly Ala
            20
```

T CELL EPITOPES OF THE CYN D 1 ALLERGEN FROM BERMUDA GRASS POLLEN

RELATED APPLICATIONS

The present application is a continuation application of Ser. No. 10/489,972, filed Sep. 15, 2004, which is a 35 U.S.C. 371 national stage filing of International Application No. PCT AU/02/01283, filed Sep. 18, 2002, which claims priority to Australian Application No. PR7754/01, filed Sep. 18, 2001. The entire contents of each of these applications are hereby incorporated by reference herein.

FIELD OF THE INVENTION

The present invention relates generally to molecules such as peptides, polypeptides and proteins which interact immunologically with T lymphocytes in subjects having Bermuda grass allergy and genetic sequences encoding same. These molecules are preferentially immunointeractive with T cells in subjects having a Bermuda grass pollen allergy. The molecules of the present invention are useful in the development of diagnostic, therapeutic and prophylactic agents for conditions characterised by an aberrant, inappropriate or otherwise unwanted immune response to Bermuda grass pollen or derivative or homologue thereof.

BACKGROUND OF THE INVENTION

Bibliographic details of the publications referred to by author in this specification are collected alphabetically at the end of the description.

The reference to any prior art in this specification is not, and should not be taken as, an acknowledgment or any form of suggestion that that prior art forms part of the common general knowledge in Australia.

Bermuda (or couch) grass (*Cynodon dactylon*) pollen is a clinically important seasonal aeroallergen in sub-tropical climates worldwide and in temperate climates where Bermuda grass is increasingly used in lawn mixes and to prevent soil erosion. In Australia, rye grass pollen is generally regarded as the most important seasonal allergen source, but of 736 patients in our allergy data base with seasonal asthma and/or rhinitis, 627 (85%) are sensitised to both BGP and rye grass pollen and only 100 (14%) are sensitised to rye grass pollen alone. Patients who have clinical seasonal allergy due to rye grass have symptoms in spring but with Bermuda grass pollen allergy peak symptoms extend into late summer in the southern hemisphere.

Pharmacotherapy is the mainstay of treatment for allergic diseases, but for appropriately chosen subjects, allergen specific immunotherapy (SIT) offers the opportunity to modify the natural course of the disease and has been shown to be highly efficacious and long-lasting in grass pollen allergy (Durham, S. R., Walker S. M., Varga, E. M., Jacobson, M. R., O'Brien, F., Novel, W., Till, S. J., Hamid, Q. A., *N. Engl. J. Med.*, 341:468-475, 1999). Nevertheless, although SIT is accepted clinical practice for treatment of seasonal rhinitis, the treatment is seldom used in asthmatic patients for fear of inducing severe asthma or even anaphylaxis. In our allergy clinic, 50% of the patients with Bermuda grass allergy experience asthma and rhinitis. Therefore there is a demand for safer SIT regimens to permit wider application for treatment of Bermuda grass pollen sensitivity. With a growing appreciation of the critical role of T cells in the elicitation and regulation of the immune response to allergens, new T cell targeted strategies for SIT are being explored. Preparations which lack IgE binding reactivity but contain dominant T cell epitopes should be safe and effective.

Previous studies have identified multiple IgE-reactive proteins of Bermuda grass pollen using sera from Bermuda grass pollen-allergic patients, with predominant humoral recognition of one protein, Cyn d 1 (>76%), thus termed the major allergen of Bermuda grass pollen (Orren, A. & Dowdle, E. B., *S. Afr. Med. J.*, 51:586-591, 1977; Ford, S. A. & Baldo, B. A., *J. Allergy Clin. Immunol.*, 79:711-720, 1987; Shen, H. D., Wang, S. R., Atang, R. B., Chang, Z. N., Han, S. H., *Clin. Allergy*, 18:401-409, 1988; Matthiesen, F., Schumacher, M. H., Løwenstein, H., *J. Allergy Clin. Immunol.*, 83:1124-1134, 1989). The cDNA encoding Cyn d 1 has been cloned and from the nucleotide sequence the primary amino acid sequence has been deduced (Smith, P. M., Suphiogl, C., Griffith, I. J., Theriault, K., Knox, R. B., Singh, M. B., *J. Allergy Clin. Immunol.*, 98:331-343, 1996). There has previously been reported an analysis of human peripheral blood T cell recognition of Bermuda grass pollen in atopic Bermuda grass pollen-allergic and non-atopic subjects (Blaher, B., McCluskey, J., Puy, R., Czarny, D., Rolland J. M., *Immunol. Cell Biol.*, 73:17-22, 1995). Both groups showed T cell proliferative responses to Bermuda grass pollen but the magnitude of response on average was greater in the atopics. Studies with other allergens indicate that a predominant Th2-type cytokine response to allergens further distinguishes those individuals with an allergic phenotype (Li, Y., Simons, E. R., Jay, F. T., HayGlass, K. T., *Int. Immunol.*, 8:897-904, 1996). Clinical efficacy of SIT is reported to be associated with decreased production of IL-4 and IL-5 by allergen-stimulated T cells (Rolland, J. & O'Hehir, R., *Curr Opin Immunol.*, 10:640-645, 1998). Therefore a thorough knowledge of allergen-specific T cell responses is required for improved SIT preparations.

T cell reactive determinants have not been reported for Bermuda grass pollen. Thus, detailed characterisation and elucidation of the immune response to Bermuda grass pollen or derivative thereof such as Cyn d 1, is critical in the development of specific diagnostic and immunotherapeutic methodology.

In work leading up to the present invention, the inventors have identified the human T cell epitopes of the Bermuda grass pollen, Cyn d 1. Further, in order to elucidate mechanisms of SIT, Bermuda grass pollen-sensitive patients were tested before and after standard immunotherapy using a tailored depot preparation containing 50% Bermuda grass pollen and 50% 7-grass mix. This preparation was used since there are minimal cross-reactive homologues between the Pooideae subfamily and Bermuda grass pollen (Marsh, D. G., Haddad, Z. H., Campbell, D. M., *J. Allergy*, 46:107-121, 1970; Martin, B. G., Mansfield, L. E., Nelson, H. S., *Ann. Allergy*, 54:99-104, 1985 and Suphioglu, C., Singh, M. B., Knox, R. B., *Int. Arch. Allergy Immunol.*, 102:144-151, 1993). Therefore the standard 7-grass mix extract (Rye, Cockfoot, Bent, Kentucky Blue, Sweet Vernal, Timothy and Meadow Fescue) frequently used for immunotherapy of grass pollen allergy is unlikely to relieve symptoms due to Bermuda grass pollen sensitisation. Using oligoclonal T cell blasts, Cyn d 1 was shown to be a major T cell allergen of Bermuda grass pollen and three highly immunogenic regions of Cyn d 1 were identified. Following successful SIT there was a marked decrease in the allergen specific T cell proliferative response accompanied by a decrease in the IL-5:IFN-γ ratio. The identification of Bermuda grass pollen T cell epitopes now facilitates the development of molecules and methodology for the diagnosis and treatment of conditions characterised by the aberrant, inappropriate or otherwise unwanted immune response to Bermuda grass pollen or derivative or homologue thereof.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The subject specification contains nucleotide sequence information prepared using the programme PatentIn Version 3.1, presented herein after the bibliography. Each amino acid sequence is identified in the sequence listing by the numeric indicator <201> followed by the sequence identifier (eg. <210>1, <210>2, etc). The length, type of sequence (Protein, etc) and source organism for each nucleotide sequence is indicated by information provided in the numeric indicator fields <211>, <212> and <213>, respectively. Amino acid sequences referred to in the specification are identified by the indicator SEQ ID NO: followed by the sequence identifier (eg. SEQ ID NO:1, SEQ ID NO:2, etc.). The sequence identifier referred to in the specification correlates to the information provided in numeric indicator field <400> in the sequence listing, which is followed by the sequence identifier (eg. <400>1, <400>2, etc). That is SEQ ID NO:1 as detailed in the specification correlates to the sequence indicated as <400>1 in the sequence listing.

One aspect of the present invention provides an isolated peptide of the formula:

$X_1X_2X_3$ wherein:
  $X_1$ and $X_3$ may be the same or different and each is an amino acid sequence comprising from 0 to 40 naturally or non-naturally occurring amino acid residues;
  $X_2$ is any amino acid sequence derived from or homologous to Cyn d 1;
and wherein said peptide molecule is capable of interacting with T cells and modifying T cell function when incubated with cells from subjects having a condition characterised by an aberrant, unwanted or otherwise inappropriate immune response to Cyn d 1 or a derivative, homologue, analogue, mutant, chemical equivalent or mimetic of said peptide.

In another aspect there is provided an isolated peptide of the formula:

$X_1X_2X_3$ wherein:
  $X_1$ and $X_3$ may be the same or different and each is an amino acid sequence comprising from 0 to 40 naturally or non-naturally occurring amino acid residues;
  $X_2$ is an amino acid sequence of from 5 to 100 residues derived from, homologous to or contiguous with amino acids 1-246 inclusive or derivatives thereof of Cyn d 1;
and wherein said peptide molecule is capable of interacting with T cells and modifying T cell function when incubated with cells from subjects having a condition characterised by an aberrant, unwanted or otherwise inappropriate immune response to Cyn d 1 or a derivative, homologue, mutant, chemical equivalent or mimetic of said peptide.

In yet another aspect the present invention provides an isolated peptide of the formula:

$X_1X_2X_3$ wherein
  $X_1$ and $X_3$ may be the same or different and each is an amino acid sequence comprising from 0 to 40 naturally or non-naturally occurring amino acid residues;
  $X_2$ is an amino acid sequence of from 5 to 100 residues derived from, homologous to or contiguous with amino acids 91-128, 163-209 or 217-246 inclusive or derivatives thereof of Cyn d 1;
and wherein said peptide molecule is capable of interacting with T cells and modifying T cell function when incubated with cells from subjects having a condition characterised by an aberrant, unwanted or otherwise inappropriate immune response to Cyn d 1 or a derivative, homologue, analogue, mutant, chemical equivalent or mimetic of said peptide.

Preferably, $X_2$ is any amino acid sequence of from 5 to 100 residues derived from, homologous to or contiguous with amino acids 91-110, 100-119, 109-128, 163-182, 172-191, 181-200, 190-209, 217-236 and/or 222-241 inclusive or derivatives thereof of Cyn d 1. Yet more particularly, $X_2$ is any amino acid sequence of from 5 to 100 residues derived from homologous to or contiguous with amino acids 109-128, 181-209 and/or 217-241 inclusive or derivatives thereof of Cyn d 1.

Most particularly, $X_2$ is any amino acid sequence of from 5 to 100 residues derived from, homologous to or contiguous with amino acids 109-128 inclusive or derivatives thereof of Cyn d 1.

$X_2$ may be any amino acid sequence of from 5 to 100 residues derived from, homologous to or contiguous with amino acids 181-200 and/or 190-209 inclusive or derivatives thereof of Cyn d 1.

$X_2$ may also be any amino acid sequence of from 5 to 100 residues derived from, homologous to or contiguous with amino acids 217-236 and/or 222-241 inclusive or derivatives thereof of Cyn d 1.

In a particularly preferred embodiment, $X_2$ comprises a sequence of at least 5 amino acids derived from one or more of the following amino acid sequences:

| | |
|---|---|
| SGKAFGAMAKKGQEDKLRKA | (SEQ ID NO: 14) |
| PKDSDEFIPMKSSWGAIWRI | (SEQ ID NO: 22) |
| MKSSWGAIWRIDPKKPLKGP | (SEQ ID NO: 23) |
| EGGAHLVQDDVIPANWKPDT | (SEQ ID NO: 26) |
| LVQDDVIPANWKPDTVYTSK | (SEQ ID NO: 27) |

More preferably, $X_2$ comprises a sequence of at least 5 amino acids derived from one or more of <400>14 or <400>26.

Another aspect of the present invention provides an isolated peptide comprising any amino acid sequence derived from or homologues to Cyn d 1 wherein said peptide molecule is capable of interacting with T cells and modifying T cell function when incubated with cells from subjects having a condition characterised by an aberrant, unwanted or otherwise inappropriate immune response to Cyn d 1 or a derivative, homologue, analogue, mutant, chemical equivalent or mimetic of said peptide.

Still another aspect of the present invention provides an isolated peptide comprising an amino acid sequence of from 5-100 residues derived from, homologues to or contiguous with amino acids 1-246 inclusive or derivatives thereof of Cyn d 1 wherein said peptide molecule is capable of interacting with T cells and modifying T cell function when incubated with cells from subjects having a condition characterised by an aberrant, unwanted or otherwise inappropriate immune response to Cyn d 1 or a derivative, homologue, analogue, mutant, chemical equivalent or mimetic of said peptide.

In another aspect the present invention provides a method for the treatment and/or prophylaxis of a condition in a subject, which condition is characterised by the aberrant, unwanted or otherwise inappropriate immune response to Cyn d 1, said method comprising administering to said subject an effective amount of a peptide as hereinbefore defined for a time and under conditions sufficient to remove or reduce the presence or function in said subject of T cells directed to said Cyn d 1.

Yet another aspect of the present invention contemplates the use of an agent as hereinbefore defined in the manufacture of a medicament for the treatment of a condition in a mammal, which condition is characterised by an aberrant, unwanted or otherwise inappropriate immune response to Cyn d 1.

In yet another further aspect, the present invention contemplates a pharmaceutical composition comprising an agent as hereinbefore defined and one or more pharmaceutically acceptable carriers and/or diluents. Said agents are referred to as the active ingredients.

Yet another aspect of the present invention relates to agents, as hereinbefore defined, when used in the method of the present invention.

A further aspect of the present invention is directed to a method of diagnosing or monitoring a condition in a mammal, which condition is characterised by an aberrant, unwanted or inappropriate response to Cyn d 1, said method comprising screening for Cyn d 1 reactive T cells utilising the peptides hereinbefore defined.

In another further aspect the present invention provides diagnostic kits for use in the diagnostic methodology hereinbefore defined.

Single and three letter abbreviations used throughout the specification are defined in Table 1.

TABLE 1

Single and three letter amino acid abbreviations

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

BRIEF DESCRIPTION OF THE DRAWINGS

FIG. 1 is a graphical representation of the visual analogue scores of patients pre- and post-SIT. (A), patients treated with two courses of SIT and (B), patients treated with one course of SIT.

FIG. 2 is a schematic representation of the amino acid sequences of the overlapping peptides (SEQ ID NOs:2-28) of Cyn d 1 (SEQ ID NO:1). Residues are indicated with the single letter code.

FIG. 3 is a graphical representation of the changes in T cell proliferation (A) and cytokine production (B) & (C) following SIT in one patient (patient 2). Proliferation pre-SIT ■ (background=2600 cpm), post 1-SIT (one course) 0 (background=4700 cpm) and post 2-SIT (two courses) (background=8000 cpm) are shown. Production of IL-5 (B) and IFN-γ (C) in culture supernatants was assessed by ELISA. Cytokine levels were measured for peptides which elicited a proliferative response ≥2.5 times background pre-SIT. Values indicate averages of duplicate samples.

FIG. 4 is a graphical representation of the changes in T cell proliferative responses to Bermuda grass pollen (A) & (B) and Cyn d 1 (C) & (D) in Bermuda grass pollen-allergic patients. The maximal response for each antigen is expressed as a stimulation index and compared pre-SIT and post-SIT [one course (post 1), two courses (post 2)].

FIG. 5 is a graphical representation of the change in frequency of recognition of peptides (SI≥2.5) following SIT in Bermuda grass pollen-allergic patients. Proliferation before SIT (A), after one course of SIT (B) and after two courses of SIT (C) are compared.

FIG. 6 is a graphical representation of the comparison of cytokine levels pre- and post-SIT (1 or 2 courses) in Bermuda grass pollen-allergic patients.

DETAILED DESCRIPTION OF THE INVENTION

The present invention is predicated, in part, on the identification of Bermuda grass pollen T cell epitopic regions. The identification of immunodominant epitopes of Bermuda grass pollen, and in particular Cyn d 1 has enabled the improvement of diagnostic methodology and the development of therapeutic and prophylactic compositions and treatment approaches for conditions such as, but not limited to, Bermuda grass pollen allergy.

In accordance with the present invention, overlapping peptides were synthesised based on the Cyn d 1 amino acid sequence disclosed in <400>1. The T cell immunoreactivity of these peptides is identified in accordance with the present invention on the basis of interactivity of peripheral blood cells or T cells obtained from the peripheral blood of subjects with severe seasonal rhinitis and/or asthma. The identification and generation of these molecules thereby form the basis for a new range of diagnostic, therapeutic and prophylactic reagents and procedures.

Accordingly, one aspect of the present invention provides an isolated peptide of the formula:

$$X_1X_2X_3$$

wherein:

$X_1$ and $X_3$ may be the same or different and each is an amino acid sequence comprising from 0 to 40 naturally or non-naturally occurring amino acid residues;

$X_2$ is any amino acid sequence derived from or homologous to Cyn d 1;

and wherein said peptide molecule is capable of interacting with T cells and modifying T cell function when incubated with cells from subjects having a condition characterised by an aberrant, unwanted or otherwise inappropriate immune response to Cyn d 1 or a derivative, homologue, analogue, mutant, chemical equivalent or mimetic of said peptide. Cyn d 1 is a protein which has been identified in Bermuda grass (also known as couch grass or *Cynodon dactylon*) pollen.

Accordingly, reference to "Cyn d 1" should be understood as including reference to all forms of Cyn d 1 or derivatives, mutants, homologues, analogues, equivalents or mimetics thereof. This includes, for example, all protein forms of Cyn d 1 or its functional equivalent or derivative including, for example, any isoforms which may arise from alternative splicing of Cyn d 1 mRNA. For instance, "Cyn d 1" should be understood to encompass the 10 Cyn d 1 isoforms described by Chang et al. (*Clin. Exp. Allergy,* 29:488-496, 1999) and the isoforms described by Smith et al (1996, supra). It includes reference to mutants, polymorphic variants or homologues of Cyn d 1. It also includes reference to analogues or equivalents of Cyn d 1 such as may occur where a product which naturally comprises Cyn d 1 is synthetically generated for the purpose of generating a product. The present invention thereby provides epitopes and methods for their use in the diagnosis and treatment of any condition characterised by hypersensitivity to a Cyn d 1 or Cyn d 1-like molecule such as Bermuda grass pollen allergies or asthma. Preferably, said Cyn d 1 comprises the sequence set forth in SEQ ID NO:1 or is a derivative, homologue, analogue, chemical equivalent, mutant or mimetic of said sequence.

The present invention therefore more particularly provides an isolated peptide of the formula:

$$X_1X_2X_3$$

wherein:
$X_1$ and $X_3$ may be the same or different and each is an amino acid sequence comprising from 0 to 40 naturally or non-naturally occurring amino acid residues;
$X_2$ is an amino acid sequence of from 5 to 100 residues derived from, homologous to or contiguous with amino acids 1-246 inclusive or derivatives thereof of Cyn d 1;
and wherein said peptide molecule is capable of interacting with T cells and modifying T cell function when incubated with cells from subjects having a condition characterised by an aberrant, unwanted or otherwise inappropriate immune response to Cyn d 1 or a derivative, homologue, mutant, chemical equivalent or mimetic of said peptide.

Still more particularly the present invention provides an isolated peptide of the formula:

$$X_1X_2X_3$$

wherein
$X_1$ and $X_3$ may be the same or different and each is an amino acid sequence comprising from 0 to 40 naturally or non-naturally occurring amino acid residues;
$X_2$ is an amino acid sequence of from 5 to 100 residues derived from, homologous to or contiguous with amino acids 91-128, 163-209 or 217-246 inclusive or derivatives thereof of Cyn d 1;
and wherein said peptide molecule is capable of interacting with T cells and modifying T cell function when incubated with cells from subjects having a condition characterised by an aberrant, unwanted or otherwise inappropriate immune response to Cyn d 1 or a derivative, homologue, analogue, mutant, chemical equivalent or mimetic of said peptide.

Still more particularly, $X_2$ is any amino acid sequence of from 5 to 100 residues derived from, homologous to or contiguous with amino acids 91-110, 100-119, 109-128, 163-182, 172-191, 181-200, 190-209, 217-236 and/or 222-241 inclusive or derivatives thereof of Cyn d 1. Yet more particularly, $X_2$ is any amino acid sequence of from 5 to 100 residues derived from homologous to or contiguous with amino acids 109-128, 181-209 and/or 217-241 inclusive or derivatives thereof of Cyn d 1.

Most particularly, $X_2$ is any amino acid sequence of from 5 to 100 residues derived from, homologous to or contiguous with amino acids 109-128 inclusive or derivatives thereof of Cyn d 1.

Still more particularly, $X_2$ is any amino acid sequence of from 5 to 100 residues derived from, homologous to or contiguous with amino acids 181-200 and/or 190-209 inclusive or derivatives thereof of Cyn d 1.

Still more particularly, $X_2$ is any amino acid sequence of from 5 to 100 residues derived from, homologous to or contiguous with amino acids 217-236 and/or 222-241 inclusive or derivatives thereof of Cyn d 1.

Reference to "T cells" should be understood as a reference to any cell comprising a T cell receptor. In this regard, the T cell receptor may comprise any one or more of the α, β, γ or δ chains. The present invention is not intended to be limited to any particular functional sub-class of T cells although in a preferred embodiment the subject T cell is a T helper cell and still more preferably a Th2-type cell, predominantly. In this regard, reference to "modifying T cell function" should be understood as a reference to modifying any one or more functions which a T cell is capable of performing. For example, the subject function may be proliferation, differentiation or other form of cellular functional activity such as the production of cytokines. Preferably, the subject functional activity is proliferation.

In terms of modifying the function of T cells from subjects having a condition characterised by an aberrant, unwanted or inappropriate immune response to Cyn d 1, it should be understood that this is not necessarily a reference to modifying the function of all the T cells in a given sample but is likely, in fact, to reflect the modification or functioning of only some of the T cells in the sample. For example, only a portion of the T helper cells in a given T cell sample may functionally respond to contact with the subject peptide. Such a partial response should be understood to fall within the scope of the present invention. It should also be understood that the T cells which are derived from the subject may be freshly harvested T cells or they may have undergone some form of in vitro or in vivo manipulation prior to testing. For example, T cell lines may have been generated from the cell sample and it is these T cell lines which then form the subject derived T cell population which is tested in accordance with the present invention. To the extent that the subject functional activity is T cell proliferation, the T cell proliferation assay is preferably performed as disclosed herein. Still more preferably, the subject modification of T cell function is the induction of a proliferation index of >2.5.

Reference to an "aberrant, unwanted or otherwise inappropriate" immune response should be understood as a reference to any form of physiological activity which involves the activation and/or functioning of one or more immune cells where that activity is inappropriate in that it is of an inappropriate type or proceeds to an inappropriate degree. It may be aberrant in that according to known immunological principals it either should not occur when it does so or else should occur when it does not do so. In another example, the immune response may be inappropriate in that it is a physiologically normal response but which is unnecessary and/or unwanted, such as occurs with respect to type-I hypersensitivity responses to innocuous allergens. Preferably said immune response is Bermuda grass pollen hypersensitivity.

Reference to "Bermuda grass pollen hypersensitivity" should be understood to mean the exhibition of clinical symptoms of IgE mediated Bermuda grass pollen hypersensitivity, for example rhinitis and/or asthma with confirmation of Bermuda grass specific IgE as determined via skin prick tests to Bermuda grass pollen extract (wheal diameters ≥5 mm) and/or using the Kallestad Allercot EAST system (Sanofi-Pasteur Diagnostics, USA) ≥Class 1 or Pharmacia UniCAP Class ≥1

In a preferred embodiment, $X_2$ comprises not less than about 5 and not greater than about 50 amino acid residues, more preferably not less than about 5 and not greater than about 30 amino acid residues and even more preferably not less than about 5 and not greater than about 20.

In a particularly preferred embodiment, $X_2$ comprises a sequence of at least 5 amino acids derived from one or more of the following amino acid sequences:

```
SGKAFGAMAKKGQEDKLRKA     SEQ ID NO: 14
PKDSDEFIPMKSSWGAIWRI     SEQ ID NO: 22
MKSSWGAIWRIDPKKPLKGP     SEQ ID NO: 23
EGGAHLVQDDVIPANWKPDT     SEQ ID NO: 26
LVQDDVIPANWKPDTVYTSK     SEQ ID NO: 26
```

More preferably, $X_2$ comprises a sequence of at least 5 amino acids derived from one or more of <400>14 or <400>26.

Reference to a "peptide" includes reference to a peptide, polypeptide or protein or parts thereof. The peptide may be glycosylated or unglycosylated and/or may contain a range of other molecules fused, linked, bound or otherwise associated to the protein such as amino acids, lipids, carbohydrates or other peptides, polypeptides or proteins. Reference hereinafter to a "peptide" includes a peptide comprising a sequence of amino acids as well as a peptide associated with other molecules such as amino acids, lipids, carbohydrates or other peptides, polypeptides or proteins.

"Derivatives" include fragments, parts, portions and variants from natural, synthetic or recombinant sources including fusion proteins. Parts or fragments include, for example, active regions of the subject peptide. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence.

Substitutional amino acid variants are those in which at least one residue in the sequence has been removed and a different residue inserted in its place. An example of substitutional amino acid variants are conservative amino acid substitutions. Conservative amino acid substitutions typically include substitutions within the following groups: glycine and alanine; valine, isoleucine and leucine; aspartic acid and glutamic acid; asparagine and glutamine; serine and threonine; lysine and arginine; and phenylalanine and tyrosine. Additions to amino acid sequences include fusions with other peptides, polypeptides or proteins.

Chemical and functional equivalents of the subject peptide should be understood as molecules exhibiting any one or more of the functional activities of these molecules and may be derived from any source such as being chemically synthesized or identified via screening processes such as natural product screening.

The derivatives include fragments having particular epitopes or parts of the entire protein fused to peptides, polypeptides or other proteinaceous or non-proteinaceous molecules.

Analogues contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecules or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acids contemplated herein is shown in Table 2.

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
| | | L-N-methylaspartic acid | Nmasp |

TABLE 2-continued

| Non-conventional amino acid | Code | Non-conventional amino acid | Code |
|---|---|---|---|
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl--aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |

TABLE 2-continued

| Non-conventional amino acid | Code | Non-conventional amino acid | Code |
|---|---|---|---|
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanin | Nmhphe |
| N-(N-(2,2-diphenylethyl)-carbamylmethyl)glycine | Nnbhm | N-(N-(3,3-diphenylpropyl)-carbamylmethyl)glycine | Nnbhe |
| 1-carboxy-1-(2,2-diphenyl-ethylamino)cyclopropane | Nmbc | | |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety.

It is possible to modify the structure of a peptide according to the invention for various purposes such as for increasing solubility, enhancing therapeutic or preventative efficacy, enhancing stability or increasing resistance to proteolytic degradation. A modified peptide may be produced in which the amino acid sequence has been altered, such as by amino acid substitution, deletion or addition, to modify immunogenicity and/or reduce allergenicity. Similarly components may be added to peptides of the invention to produce the same result.

For example, a peptide can be modified so that it exhibits the ability to induce T cell anergy. In this instance, critical binding residues for the T cell receptor can be determined using known techniques (for example substitution of each residue and determination of the presence or absence of T cell reactivity). In one example, those residues shown to be essential to interact with the T cell receptor can be modified by replacing the essential amino acid with another, preferably similar amino acid residue (a conservative substitution) whose presence is shown to alter T cell reactivity or T cell functioning. In addition, those amino acid residues which are not essential for T cell receptor interaction can be modified by being replaced by another amino acid whose incorporation may then alter T cell reactivity or T cell functioning but does not, for example, eliminate binding to relevant MHC proteins.

Such modifications will result in the production of molecules falling within the scope of "mutants" of the subject peptide as herein defined. "Mutants" should be understood as a reference to peptides which exhibit one or more structural features or functional activities which are distinct from those exhibited by the non-mutated peptide counterpart.

Peptides of the invention may also be modified to incorporate one or more polymorphisms resulting from natural allelic variation and D-amino acids, non-natural amino acids or amino acid analogues may be substituted into the peptides to produce modified peptides which fall within the scope of the invention. Peptides may also be modified by conjugation with polyethylene glycol (PEG) by known techniques. Reporter groups may also be added to facilitate purification and potentially increase solubility of the peptides according to the invention. Other well known types of modification including insertion of specific endoprotease cleavage sites, addition of functional groups or replacement of hydrophobic residues with less hydrophobic residues as well as site-directed mutagenesis of DNA encoding the peptides of the invention may also be used to introduce modifications which could be useful for a wide range of purposes. The various modifications to peptides according to the invention which have been mentioned above are mentioned by way of example only and are merely intended to be indicative of the broad range of modifications which can be effected.

Another aspect of the present invention provides an isolated peptide comprising any amino acid sequence derived from or homologues to Cyn d 1 wherein said peptide molecule is capable of interacting with T cells and modifying T cell function when incubated with cells from subjects having a condition characterised by an aberrant, unwanted or otherwise inappropriate immune response to Cyn d 1 or a derivative, homologue, analogue, mutant, chemical equivalent or mimetic of said peptide.

More particularly, the present invention provides an isolated peptide comprising an amino acid sequence of from 5-100 residues derived from, homologues to or contiguous with amino acids 1-246 inclusive or derivatives thereof of Cyn d 1 wherein said peptide molecule is capable of interacting with T cells and modifying T cell function when incubated with cells from subjects having a condition characterised by an aberrant, unwanted or otherwise inappropriate immune response to Cyn d 1 or a derivative, homologue, analogue, mutant, chemical equivalent or mimetic of said peptide.

In one preferred embodiment said amino acid sequence is derived from, homologous to or contiguous with amino acids 91-128, 163-209 or 217-246 inclusive or derivatives thereof of Cyn d 1.

In another preferred embodiment said amino acid sequence is derived from, homologous to or contiguous with amino acids 91-110, 100-119, 109-128, 163-182, 172-191, 181-200, 190-209, 217-236 and/or 222-241 inclusive or derivatives thereof of Cyn d 1. In yet another preferred embodiment said amino acid sequence is derived from, homologous to or contiguous with amino acids 109-128, 181-209 and/or 217-241 inclusive or derivatives thereof of Cyn d 1.

In another aspect said amino acid sequence comprises a sequence of at least 5 amino acids derived from one or more of the following amino acid sequences:

```
SGKAFGAMAKKGQEDKLRKA      SEQ ID NO: 14
PKDSDEFIPMKSSWGAIWRI      SEQ ID NO: 22
MKSSWGAIWRIDPKKPLKGP      SEQ ID NO: 23
EGGAHLVQDDVIPANWKPDT      SEQ ID NO: 26
LVQDDVIPANWKPDTVYTSK      SEQ ID NO: 27
```

According to this aspect, said amino acid sequence preferably comprises a sequence of at least 5 amino acids derived from one or more of <400>14 or <400>26.

The peptides of the present invention may be prepared by recombinant or chemical synthetic means. According to a preferred aspect of the present invention, there is provided a recombinant peptide which is preferentially immunologically reactive with T cells from individuals with Bermuda Grass pollen hypersensitivity, which is expressed by the expression of a host cell transformed with a vector coding for the peptide sequence of the present invention. The peptide may be fused to another peptide, polypeptide or protein. Alternatively, the peptide may be prepared by chemical synthetic techniques, such as by the Merrifield solid phase synthesis procedure. Furthermore, although synthetic peptides of the formula given above represent a preferred embodiment, the present invention also extends to biologically pure preparations of the naturally occurring peptides or fragments thereof. By "biologically pure" is meant a preparation comprising at least about 60%, preferably at least about 70%, or preferably at least about 80% and still more preferably at least about 90% or greater as determined by weight, activity or other suitable means.

In another aspect it may be particularly useful to generate a mutant peptide comprising T cell epitopic regions but which peptides lack B cell epitopes capable of interacting with IgE. Such peptides may be generated by synthesising peptides comprising only T cell epitopes or by mutating naturally occurring molecules such that the T cell epitopes remain functional while the B cell epitopes are altered to prevent antibody binding.

The present invention should therefore be understood to encompass peptides that comprise at least one B or T cell epitope of Cyn d 1 in conjunction with other amino acids (which may or may not be naturally occurring as amino acid analogues) or other chemical species. In a preferred aspect of the invention such peptides may comprise one or more epitopes of Cyn d 1, which epitopes may be T or B cell epitopes. Peptides with one or more T cell epitopes of Cyn d 1 are desirable for increased therapeutic effectiveness.

In another aspect, the present invention provides a nucleic acid molecule comprising a sequence of nucleotides encoding or complementary to a sequence encoding the peptides as hereinbefore defined or a derivative, homologue or analogue thereof. It should be understood that reference to "peptides" includes reference to peptides comprising one or more T cell epitopes. A nucleic acid molecule encoding the subject peptide is preferably a sequence of deoxyribonucleic acids such as cDNA or a genomic sequence. A genomic sequence may comprise exons and introns. A genomic sequence may also include a promoter region or other regulatory regions.

The nucleic acid molecule may be ligated to an expression vector capable of expression in a prokaryotic cell (eg. E. coli) or a eukaryotic cell (eg. yeast cells, fungal cells, insect cells, mammalian cells or plant cells). The nucleic acid molecule may be ligated or fused or otherwise associated with a nucleic acid molecule encoding another entity such as, for example, a signal peptide. It may also comprise additional nucleotide sequence information fused, linked or otherwise associated with it either at the 3' or 5' terminal portions or at both the 3' and 5' terminal portions. The nucleic acid molecule may also be part of a vector, such as an expression vector. The latter embodiment facilitates production of recombinant forms of the subject peptide which forms are encompassed by the present invention.

Such nucleic acids may be useful for recombinant production of T cell epitopes of Cyn d 1 or proteins comprising them by insertion into an appropriate vector and transfection into a suitable cell line. Such expression vectors and host cell lines also form an aspect of the invention.

In producing peptides by recombinant techniques, host cells transformed with a nucleic acid having a sequence encoding a peptide according to the invention or a functional equivalent of the nucleic acid sequence are cultured in a medium suitable for the particular cells concerned. Peptides can then be purified from cell culture medium, the host cells or both using techniques well known in the art such as ion exchange chromatography, gel filtration chromatography, ultrafiltration, electrophoresis or immunopurification with antibodies specific for the peptide.

Nucleic acids encoding Cyn d 1 or peptides comprising T and/or B cell epitopes of Cyn d 1 may be expressed in bacterial cells such as E. coli, insect cells, yeast or mammalian cells such as Chinese hamster ovary cells (CHO). Suitable expression vectors, promoters, enhancers and other expression control elements are referred to in Sambruck et al (Cold Spring Harbour Laboratory Press, 1989). Other suitable expression vectors, promoters, enhancers and other expression elements are well known to those skilled in the art. Examples of suitable expression vectors in yeast include Yep Sec 1 (Balderi et al., 1987, Embo. J., 6:229-234); pMFa (Kurjan and Herskowitz, Cell, 30:933-943, 1982); JRY88 (Schultz et al., Gene, 54:113-123, 1987) and pYES2 (Invitrogen Corporation, San Diego, Calif.). These vectors are freely available as are baculovirus and mammalian expression systems. For example, a baculovirus system is commercially available (ParMingen, San Diego, Calif.) for expression in insect cells while the pMsg vector is commercially available (Pharmacia, Piscataway, N.J.) for expression in mammalian cells.

For expression in E. coli suitable expression vectors include among others, pTrc (Amann et al, Gene, 69:301-315, 1988) pGex (Amrad Corporation, Melbourne, Australia); pMal (N.E. Biolabs, Beverley, Mass.); pRit5 (Pharmacia, Piscataway, N.J.); pEt-11d (Novagen, Maddison, Wis.) (Jameel et al., J. Virol., 64:3963-3966 1990) and pSem (Knapp et al., Bio Techniques, 8:280-281, 1990). The use of pTRC, and pEt-11d, for example, will lead to the expression of unfused protein. The use of pMal, pRit5, pSem and pGex will lead to the expression of allergen fused to maltose E binding protein (pMal), protein A (pRit5), truncated—galactosidase (PSEM) or glutathione S-transferase (pGex). When a T cell epitope of Cyn d 1 or a peptide comprising it is expressed as a fusion protein, it is particularly advantageous to introduce an enzymatic cleavage site at the fusion junction between the carrier protein and the peptide concerned. The peptide of the invention may then be recovered from the fusion protein through enzymatic cleavage at the enzymatic site and biochemical purification using conventional techniques for purification of proteins and peptides. Examples of enzymatic cleavage sites include those for blood clotting factor Xa or thrombin for which the appropriate enzymes and protocols for cleavage are commercially available. The different vectors also have different promoter regions allowing constitutive or inducible expression or temperature induction. It may additionally be appropriate to express recombinant peptides in different E. coli hosts that have an altered capacity to degrade recombinantly expressed proteins. Alternatively, it may be advantageous to alter the nucleic acid sequence to use codons preferentially utilised by E. coli, where such nucleic acid alteration would not effect the amino acid sequence of the expressed proteins.

Host cells can be transformed to express the nucleic acids of the invention using conventional techniques such as calcium phosphate or calcium chloride co-precipitation, DEAE-dextran-mediated transfection or electroporation. Suitable methods for transforming the host cells may be found in (Sambruck et al., 1989), and other laboratory texts. The nucleic acid sequence of the invention may also be chemically synthesised using standard techniques.

In addition to recombinant production of peptides according to the invention, the nucleic acids may be utilised as probes for experimental or purification purposes.

The identification of T cell epitopic regions facilitates the identification and/or rational design of a range of mutant peptide molecules. As detailed hereinbefore, these mutant peptides may comprise one or more mutated B cell epitopes. However there is provided scope for the generation of mutant peptides comprising mutated B cell epitopes or combinations of intact versus mutated B and T cell epitopes. The applications of these molecules are described in more detail below but in a preferred embodiment relate to modulation of the Cyn d 1 hypersensitivity immune response in terms of either a prophylactic or therapeutic treatment.

Identification and synthesis of the Cyn d 1 T cell epitopes as disclosed herein now facilitates the development of a range of diagnostic and prophylactic/therapeutic treatment protocols for use with respect to Cyn d 1 related immune conditions. Also facilitated is the development of reagents for use therein. Accordingly, the present invention should be understood to extend to the use of the peptides and monoclonal antibodies or derivatives, homologues, analogues, mutants, chemical equivalents or mimetics thereof in the therapeutic and/or prophylactic treatment of patients. Such methods of treatment include, but are not limited to:

(i) Administration of the subject peptides to a patient as a means of desensitising or inducing immunological tolerance to Cyn d 1 or Cyn d 1-like molecules. This may be achieved, for example, by inducing Cyn d 1 directed Th2 anergy or apoptosis. Such an outcome may be achieved by any one of a number of techniques including the use of peptides which maintain T cell epitope reactivity but which either naturally or as a result of mutation are unable to undergo IgE binding. Alternatively, one may utilise desensitisation/treatment protocols which are based on the administration of specific concentrations of a given peptide in accordance with a specific regime in order to induce tolerance. Such methodology may eliminate Cyn d 1 hypersensitivity or it may reduce the severity of Cyn d 1 hypersensitivity.

Preferably such treatment regimes are capable of modifying the T cell response or both the B and T cell response of the individual concerned. As used herein, modification of the allergic response of the individual suffering from Cyn d 1 hypersensitivity can be defined as inducing either non-responsiveness or diminution in symptoms to the Cyn d 1 molecule as determined by standard clinical procedures (Varney et al., *British Medical Journal*, 302:265-269, 1990). Diminution in the symptoms includes any reduction in an allergic response in an individual to Cyn d 1 after a treatment regime has been completed. This diminution may be subjective or clinically determined, for example by using standard skin tests known in the art.

Exposure of an individual to the peptides of the present invention, which peptides comprise at least one T cell epitope, may tolerise or anergise appropriate T cell subpopulations such that they become unresponsive to Cyn d 1 and do not participate in stimulating an immune response upon such exposure. Preferably the peptides according to the invention will retain immunodominant T cell epitopes but possess abrogated IgE binding.

Administration of a peptide of the invention may modify the cytokine secretion profile as compared with exposure to naturally occurring Cyn d 1 allergen. This exposure may also influence T cell subpopulations which normally participate in the allergic response to migrate away from the site or sites of normal exposure to the allergen and towards the site or sites of therapeutic administration. This redistribution of T cell subpopulations may ameliorate or reduce the ability of an individual's immune system to stimulate the usual immune response at the site of normal exposure to the allergen, resulting in diminution of the allergic symptoms.

Modification of the B cell response may be achieved, for example, via modulation of the cytokine profile produced by T cells, as detailed above. Specifically, decreasing T cell derived IL-4 and IL-13 production thereby decreasing IgE synthesis.

(ii) The peptides of the present invention may be used in the capacity of an adsorbent to remove Cyn d 1 directed T cells from a biological sample or from a patient.

Accordingly, in another aspect the present invention provides a method for the treatment and/or prophylaxis of a condition in a subject, which condition is characterised by the aberrant, unwanted or otherwise inappropriate immune response to Cyn d 1, said method comprising administering to said subject an effective amount of a peptide as hereinbefore defined for a time and under conditions sufficient to remove or reduce the presence or function in said subject of T cells directed to said Cyn d 1.

Preferably said condition is Bermuda grass pollen hypersensitivity.

An "effective amount" means an amount necessary at least partly to attain the desired immune response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials.

The subject of the treatment or prophylaxis is generally a mammal such as but not limited to human, primate, livestock animal (e.g. sheep, cow, horse, donkey, pig), companion animal (e.g. dog, cat), laboratory test animal (e.g. mouse, rabbit, rat, guinea pig, hamster), captive wild animal (e.g. fox, deer). Preferably the mammal is a human or primate. Most preferably the mammal is a human.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

Still another aspect of the present invention is directed to antibodies to Cyn d 1 including catalytic antibodies or derivatives, homologues, analogues, mutants, chemical equivalents or mimetics of said antibodies. Such antibodies may be monoclonal or polyclonal and may be selected from naturally occurring antibodies to Cyn d 1 or may be specifically raised to Cyn d 1. In the case of the latter, Cyn d 1 may first need to be associated with a carrier molecule. The antibodies and/or recombinant Cyn d 1 of the present invention are particularly useful as therapeutic or diagnostic agents. Alternatively, fragments of antibodies may be used such as Fab fragments or Fab'$_2$ fragments. Furthermore, the present invention extends to recombinant and synthetic antibodies and to antibody hybrids. A "synthetic antibody" is considered herein to include fragments and hybrids of antibodies. Cyn d 1 can also be used to screen for naturally occurring antibodies to Cyn d 1.

Both polyclonal and monoclonal antibodies are obtainable by immunization with Cyn d 1 or derivative, homologue, analogue, mutant, chemical equivalent or mimetic thereof and either type is utilizable for immunoassays. The methods of obtaining both types of sera are well known in the art. Polyclonal sera are less preferred but are relatively easily prepared by injection of a suitable laboratory animal with an effective amount of Cyn d 1, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman, Basic Facts about Hybridomas, in *Compendium of Immunology* Vol II, ed. by Schwartz, 1981; Kohler and Milstein, *Nature* 256: 495-499, 1975; *European Journal of Immunology* 6: 511-519, 1976).

Preferably, the antibody of the present invention specifically binds Cyn d 1 or derivative, homologue, analogue, mutant, chemical equivalent or mimetic thereof. By "specifically binds" is meant high avidity and/or high affinity binding of an antibody to a specific antigen. Antibody binding to its epitope on this specific antigen is stronger than binding of the same antibody to any other epitope, particularly those that may be present in molecules in association with, or in the same sample, as the specific antigen of interest. Antibodies that bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the polypeptide of interest, e.g. by use of appropriate controls.

Administration of a peptide or antibody of the present invention (herein referred to as "agent") in the form of a pharmaceutical composition, may be performed by any convenient means. The agent of the pharmaceutical composition is contemplated to exhibit therapeutic activity when administered in an amount which depends on the particular case. The variation depends, for example, on the human or animal and the agent chosen. A broad range of doses may be applicable. Considering a patient, for example, from about 0.1 mg to about 1 mg of an agent may be administered per kilogram of body weight per day. Dosage regimes may be adjusted to provide the optimum therapeutic response. For example, several divided doses may be administered daily, weekly, monthly or other suitable time intervals or the dose may be proportionally reduced as indicated by the exigencies of the situation.

The agent may be administered in a convenient manner such as by the oral, intravenous (where water soluble), intraperitoneal, intramuscular, subcutaneous, intradermal, intranasal, sublingual or suppository routes or implanting (e.g. using slow release molecules). The agent may be administered in the form of pharmaceutically acceptable nontoxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

In accordance with these methods, the agent defined in accordance with the present invention may be coadministered with one or more other compounds or molecules. By "coadministered" is meant simultaneous administration in the same formulation or in two different formulations via the same or different routes or sequential administration by the same or different routes. By "sequential" administration is meant a time difference of from seconds, minutes, hours or days between the administration of the two types of molecules. These molecules may be administered in any order.

Another aspect of the present invention contemplates the use of an agent as hereinbefore defined in the manufacture of a medicament for the treatment of a condition in a mammal, which condition is characterised by an aberrant, unwanted or otherwise inappropriate immune response to Cyn d 1.

Preferably said condition is Bermuda grass pollen hypersensitivity.

In yet another further aspect, the present invention contemplates a pharmaceutical composition comprising an agent as hereinbefore defined and one or more pharmaceutically acceptable carriers and/or diluents. Said agents are referred to as the active ingredients.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 µg and 2000 mg of active compound.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The pharmaceutical composition may also comprise genetic molecules such as a vector capable of transfecting target cells where the vector carries a nucleic acid molecule encoding a modulatory agent. The vector may, for example, be a viral vector.

Yet another aspect of the present invention relates to agents, as hereinbefore defined, when used in the method of the present invention.

In yet another aspect, the present invention should be understood to extend to the use of the peptides of the present invention in diagnostic applications. Said diagnostic applications include, but are not limited to:
  (i) To measure the reactivity of a subject's cells to Cyn d 1. This is of use, for example, with respect to the diagnosis and/or monitoring of conditions characterised by an aberrant, unwanted or otherwise inappropriate immune response to Cyn d 1. The peptides may be added into solution or bound to a solid support together with cells derived from peripheral blood or from tissue biopsies either unfractionated, fractionated or derived as a continuous cell line. Reactivity to the subject peptide may then be measured by standard proliferation assays such as incorporation of $H^3$-thymidine, measurement of expressed or secreted molecules such as surface markers, cytokines or other standard assays of cellular activity which are well known in the art.
  (ii) The use of T cell epitope comprising peptides together with a T cell proliferation assay which utilises a T cell sample derived from the subject will facilitate, for example, the identification of a T cell responsive population.

Methods of detecting Cyn d 1 may be utilised, for example, to qualitatively or quantitatively detect Cyn d 1 levels. However, these methods may also be utilised to screen for mutations or polymorphisms in Cyn d 1 which mutations may result in, for example, loss of T cell reactivity to Cyn d 1. These methods may be utilised for the purpose of screening for peptide molecules suitable for use in therapeutically or prophylactically treating an individual suffering from Cyn d 1 related hypersensitivity.

Accordingly, yet another aspect of the present invention is directed to a method of diagnosing or monitoring a condition in a mammal, which condition is characterised by an aberrant, unwanted or inappropriate response to Cyn d 1, said method comprising screening for Cyn d 1 reactive T cells utilising the peptides hereinbefore defined.

Preferably said condition is Bermuda grass pollen hypersensitivity.

In another embodiment the present invention provides diagnostic kits for use in the diagnostic methodology hereinbefore defined.

The present invention will now be further described with reference to the following non-limiting Examples.

EXAMPLE 1

Oligoclonal Analysis of the Atopic T Cell Response to the Group 1 Allergen of *Cynodon Dactylon*

Materials and Methods

Patients and Immunotherapy Protocol

Fourteen patients (8F and 6M of mean age 33.4 years) from the Asthma and Allergy Clinic, Alfred Hospital, Melbourne, Australia were studied (Table 3). All patients suffered from severe seasonal rhinitis and/or asthma with symptoms extending into late summer corresponding to the peak of the BPG season. Bermuda grass pollen-specific IgE was present in all subjects as determined by positive skin prick tests to Bermuda grass pollen extract (wheal diameters ≥5 mm) as well as positive enzyme allergosorbent test (EAST, Kallestad Allercoat Sanofi-Pasteur Diagnostics; Table 3).

Patients were administered subcutaneous allergen immunotherapy with two-weekly injections of an alum precipitated depot preparation containing 50% Bermuda grass pollen+50% 7-grass mix (Allpyral$^R$ specifically prepared and generously provided by Bayer Australia Ltd.) for twenty weeks out of the pollen season, according to the Alfred Hospital standard regimen (cumulative antigen dose 15,570 PNU per year). Heparinized peripheral blood was obtained from all patients during the pollen season before initiation of desensitization (n=14), following one year of treatment (n=14) and after two years of treatment (n=7). Changes in clinical symptomatology were documented using visual analogue scores completed by the patients (100% equals most severe symptoms and 0% equals no symptoms; FIG. 1) and by patient reported changed in medication usage. Approval was obtained from the Alfred Hospital Ethics Committee with informed written consent from each patient. Daily pollen counts were kindly provided by the School of Botany, University of Melbourne.

MHC Class II Typing

HLA-DRB1, DQB1 and DPB1 allele typing was performed using the standard methods outlined in the 11th International Histocompatibility Workshop (Kimura, A. Sasazuki, T., Oxford University Press, 1991). Briefly, exon two polymorphism was determined using a series of biotinylated oligonucleotide probes that were hybridised to PCR amplified DNA immobilised on nylon membranes. Complementary probes were detected using a streptavidin-alkaline phosphatase conjugate and the chemiluminescent substrate CDP-Star (Roche Diagnostics Pty Ltd). DPB1 hybridisation was preceded by a Sequence Specific Priming (SSP) to divide DPB1 alleles into six groups based on polymorphism at amino acid positions 8-9 and 84-85 (Varney, M. D., Tait, B. D., *Eur. J. Immunogenetics,* 25:371-374, 1998). For each loci new probes and primers were added to cover sequence polymorphism not described in the original protocol.

Antigens (i) Bermuda grass pollen.

Bermuda grass pollen was purchased from Greer Laboratories Inc. (Lenoir, N.C., USA) as dry, non-defatted pollen. One gram of pollen was extracted in 5 ml of 1 mM $NH_4HCO_3$ overnight at 4° C. on a rotating wheel. After centrifugation, the supernatant was dialyzed against PBS overnight. The extract was filtered through a 0.2 µm filter. The protein content of the extract was determined using the Bio-Rad Microassay (Bio-Rad, USA).

(ii) Cyn d 1.

Cyn d 1 was generated by the Bermuda grass pollen extract first undergoing an 80% ammonium sulphate precipitation. The supernatant from the precipitation was then passed through a G-75 Sephadex gel column (Pharmacia, Sweden). The fractions containing Cyn d 1 were pooled following analysis on SDS-PAGE and immunoblotting using a Cyn d 1-specific monoclonal antibody (3A2) (Smith et al., 1994). The protein content was determined using the Bio-Rad Microas say.

(iii) Peptides.

Synthetic peptides (20-mers overlapping by 11 or, for the two N-terminal peptides, 15 residues) spanning the entire length of the Cyn d 1 molecule were purchased from Mimotopes (Clayton, Australia; FIG. 2) (CD1 isoform, Smith et al., 1996, supra).

(iv) Mitogenicity and Toxicity.

Mitogenicity of Bermuda grass pollen, Cyn d 1 and Cyn d 1 peptides was excluded by culturing with oligoclonal house dust mite-reactive $CD4^+$ T cells in the presence of irradiated peripheral blood mononuclear cells (PBMC), and toxicity was excluded by co-culture of antigens with the HDM-reactive T cells in the presence of IL-2 (data not shown).

Generation of Bermuda Grass Pollen-Specific T Cell Lines

Bermuda grass pollen-specific T cell lines were isolated with the use of our well-established methods for thegeneration of allergen-specific T cell populations (O'Hehir, R. E., Young, D. B., Kay, A. B., Lamb, J. R., *Immunology,* 62:635-640, 1987; O'Hehir, R. E., Askonas, B. A., Lamb, J. R., Vol 3, Heidelberg:Springer-Verlag, p 120-138, 1993). Briefly, PBMC were separated from heparinized venous blood by density gradient centrifugation over Ficoll Paque (Pharmacia, Sweden). PBMC were initially stimulated for 1 week in 24-well plates (Costar, USA; $2.5 \times 10^6$ PBMC/well) with a previously determined optimal concentration of Bermuda grass pollen extract (50 µg/ml) for 7 days in complete medium (RPMI-1640 medium, Gibco Life Technologies, supplemented with 2 mmol/L L-glutamine, 100 IU/ml penicillin/streptomycin, and 5% screened, heat inactivated human $AB^+$ serum, Sigma Chemical Company, USA) at 37° C., 5% $CO_2$. A two week line was established by restimulating the T cell blasts with Bermuda grass pollen extract in the presence of irradiated (3000 rads) autologous PBMC every 7 days, with the addition of interleukin-2 (5% vol/vol; Lymphocult-TLF, Biotest Folex, Frankfurt, Germany) every 3-4 days. In all experiments, T cells were rested for 7 days after the last addition of antigen and antigen presenting cells (APC) before use in proliferation assays. We have previously shown that CD4+ T cells are preferentially expanded in these cultures.

Oligoclonal T Cell Proliferation Assays

Oligoclonal T cell blasts ($5 \times 10^4$/well) from the Bermuda grass pollen-specific T cell lines were stimulated in triplicate with Bermuda grass pollen extract (25, 50, 100 µg/ml), purified Cyn d 1 (2.5, 5, 10 µg/ml) and the Cyn d 1 peptides (1, 10 µg/ml) in the presence of an equal number of irradiated autologous PBMC as APC for 72 hours in 96-well round bottom plates (ICN Biomedicals, USA). Cultures of T cells and APC in the absence of antigen or with added IL-2 were included as negative and positive controls respectively. After 72 hours, cultures were pulsed with 1 µCi/well of tritiated methyl thymidine ($^3$HTdR; Amersham, USA) and harvested 16 hours later onto glass fibre filters. Proliferation as correlated with $^3$HTdR incorporation was measured by liquid scintillation spectroscopy. Results are expressed as change in mean counters per minute above background (Acpm) or as a stimulation index (SI, cpm of antigen stimulated T cells divided by cpm of unstimulated T cells) to allow easier comparison between subjects with different background incorporation. Stimulation index values ≥2.5 are considered significant. Production of IL-5 and IFN-γ by Bermuda grass pollen-specific oligoclonal T cells Production of IL-5 and IFN-γ by cultured oligoclonal T cells was assessed by harvesting supernatants from proliferation assays at 48 hours after stimulation, with replacement by an equal volume of complete medium, and measurement of cytokine levels by sandwich ELISA. White 96-well maxisorp ELISA plates (Nalgene NUNC, Denmark) were coated with rat anti-mouse/human IL-5 (PharMingen, USA) or mouse anti-human IFN-γ (endogen, USA) at 2 µg/ml and incubated overnight at 4° C. The plates were washed with 0.5% Tween 20/PBS and blocked with 1% BSA/PBS for 1 hour at room temperature. The plates were washed again and the culture supernatants from pooled triplicate assays added in duplicate to the wells. A standard curve was established using known concentrations of human recombinant IL-5 (PharMingen, USA) and IFN-γ (Endogen, USA). The plates were incubated with either 1 µg/ml biotinylated rat anti-human IL-5 (PharMingen, USA) or 0.5 µg/ml biotinylated mouse anti-human IFN-γ (Endogen, USA) for 1 hour at room temperature. After washing the plates, streptavidin-biotinylated horseradish peroxidase (Amersham, USA), at a dilution of 1:2000, was added to each well and incubated for 45 minutes at room temperature. The plates were once again washed and 100 µl of the ECL Chemiluminescence reagent (NEN Life Science Products, USA), made up by mixing one part enchanced luminol reagent with one part oxidizing reagent, was added to each well. The plates were read on a LumiCount microplate glow luminometer (Packard Instrument Company, USA). Standard curve construction and determination of cytokine levels was performed using Packard I-Smart software. The lower limit of detection of the IL-5 and IFN-γ assays was 10 pg/ml.

Statistics

Statistical significance of differences between results obtained at various time points of SIT was analysed by a Wilcoxon Signed Rank test. The tests with p values of less than 0.05 were considered significant.

EXAMPLE 2

Clinical Efficacy of Immunotherapy

All fourteen patients demonstrated a marked improvement in their symptoms as assessed by the visual analogue scores reported by the patients during the pollen season (FIG. 1). This was accompanied by decreased medication usage in all patients. Despite the clinical efficacy, as anticipated from published studies (Lichtenstein, L. M., Ishizaka, K., Norman, P. S., Sobotka, A. K., Hill, B. M., *J. Clin. Invest.*, 52:472-482m 1973; Gleich, G. J., Zimmerman, E. M., Henderson L. L. and Yunginger, J. W., *J. Allergy Clin. Immunol.*, 70:261-271, 1982; Creticos, P. S., Van Metre T. E., Mardiney, M. R., *J. Allergy Clin. Immunol.*, 73:94-104, 1984; Djurup, R., Malling, H., Sondergaard, I., Weeke, B., *J. Allergy. Clin. Immunol.*, 76:46-55, 1985), the Bermuda grass pollen-specific IgE measurements showed no consistent changes during the time of study (Table 2). Daily seasonal pollen counts were comparable over the three seasons.

EXAMPLE 3

Oligoclonal T Cell Respnses to Bermuda Grass Pollen Allergens

The 2-week Bermuda grass pollen-specific T cell lines from all 14 Bermuda grass pollen allergic patients showed strong proliferative T cell responses to the crude Bermuda grass pollen extract pre-immunotherapy with 13/14 patients also responding to Cyn d 1. A representative proliferation assay expressed as Acpm for one patient is shown in detail in FIG. 3A. Following SIT, thee was a marked decrease in proliferative responses to Bermuda grass pollen and Cyn d 1. Proliferation to Bermuda grass pollen following one year of SIT was decreased in 12/14 patients (FIG. 4A, B). Patient 5 showed a light decrease in proliferation after one year of SIT but interestingly T cell reactivity to Bermuda grass pollen was increased after two years. Patient 11 showed a similar increase in T cell recognition of Bermuda grass pollen at one year. A decrease in proliferation to Cyn d 1 was observed in 11/13 Cyn d 1-reactive patients following one year of SIT (FIG. 4C, D). After two years of SIT, only minimal antigen-specific T cell proliferation was observed. This was not due to induction of cytolysis, as at all three time points strong proliferation to IL-2 was observed (FIG. 3A).

EXAMPLE 4

Epitope Mapping of Cyn d 1

To identify the highly immunogenic regions of Cyn d 1, proliferative responses of oligoclonal T cells to the synthetic Cyn d 1 peptides were examined pre-immunotherapy. T cell reactivity to one or more Cyn d 1 peptides was identified in all 13 Cyn d 1-reactive patients, but the pattern of T cell recognition differed between individuals. There was no peptide recongition by the Cyn d 1-non-reactive patient. Four peptides [Cyn d 1(10-29), (46-65), (55-74) and (199-218)] failed to elicit proliferation in any subject. Regions of high immunogenicity were detected in that five peptides elicited proliferation in 6 or more patients; peptides Cyn d 1(109-128) and (217-236) each elicited responses in 8 patients and peptides Cyn d 1 (181-200), (190-209) and (222-241) each induced T cell responses in 6 patients (FIG. 5A).

HLA DRB1, DQB1 and DPB1 allele frequencies in 13/14 patients were compared to those observed in a healthy control population and for associations with a response to one or more particular peptide sequences. No unequivocal HLA associations were observed.

Figure 5:
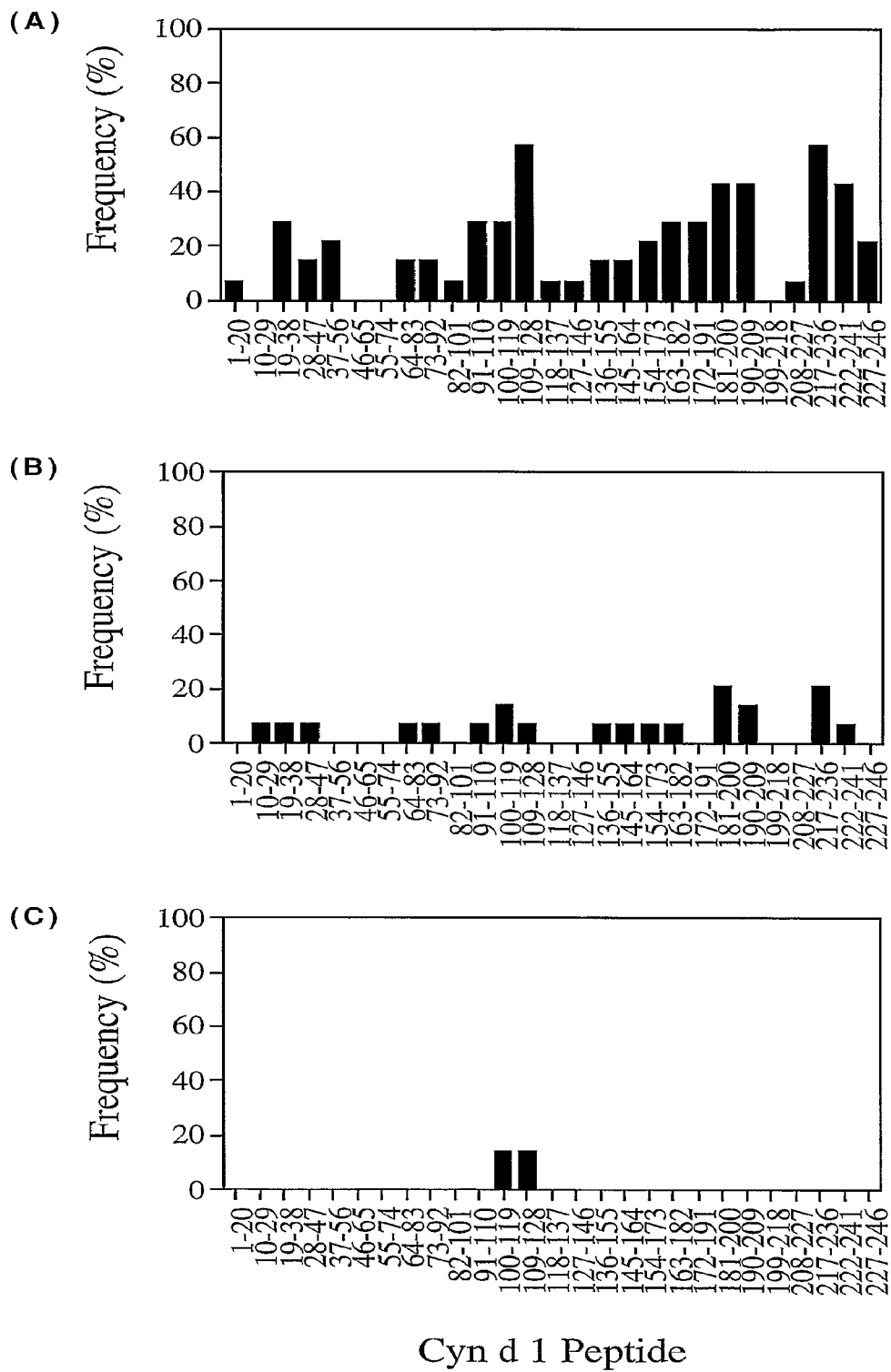

As observed with unfractionated Bermuda grass pollen extract and Cyn d 1, following SIT, recognition of the Cyn d 1 peptides decreased markedly (FIG. 5), with negligible determinant spreading. For the 7 patients who had 2 years of SIT, only 2 peptides elicited a proliferative response, each in two patients (FIG. 5C).

EXAMPLE 5

Cytokine Profile of Reactive T Cells

Figure 3:
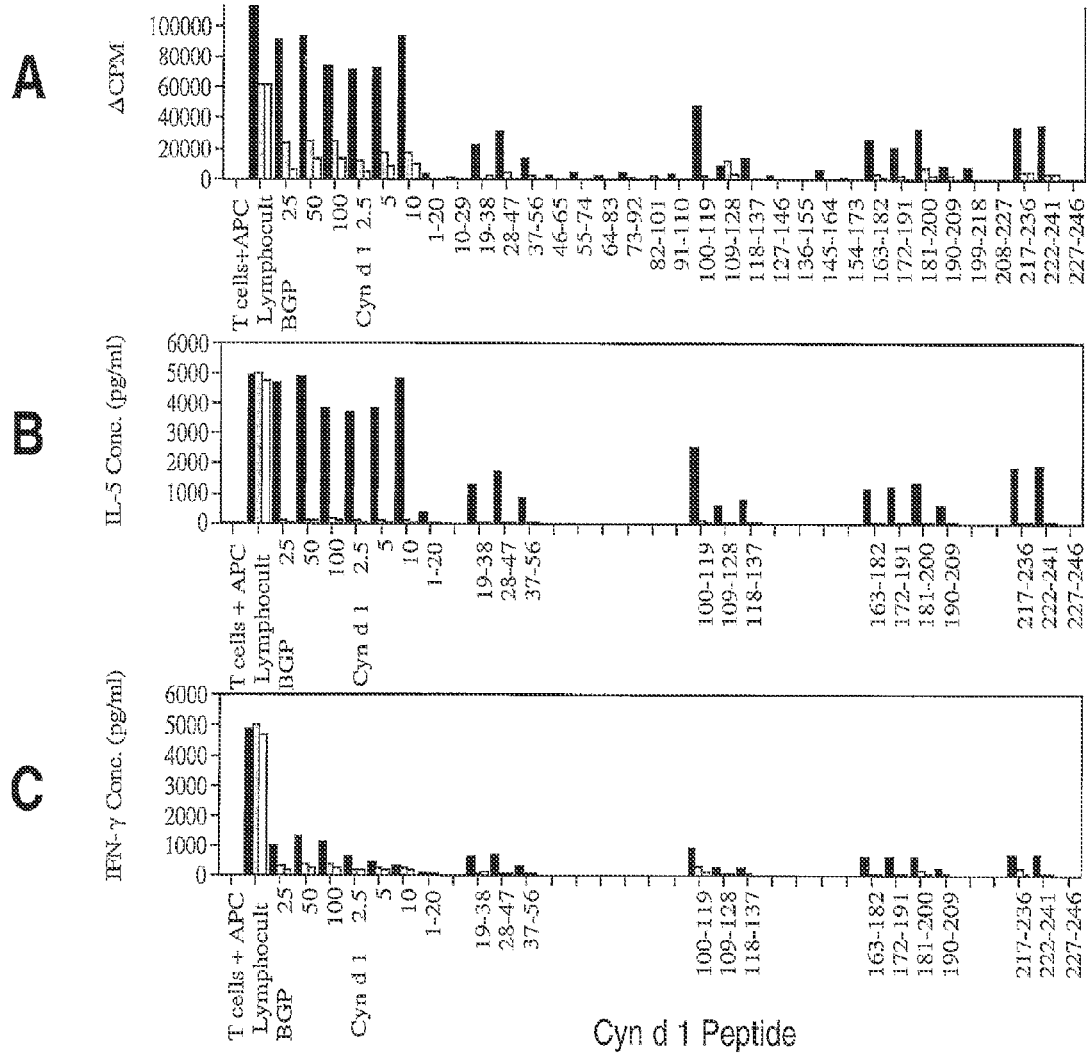
Figure 4:
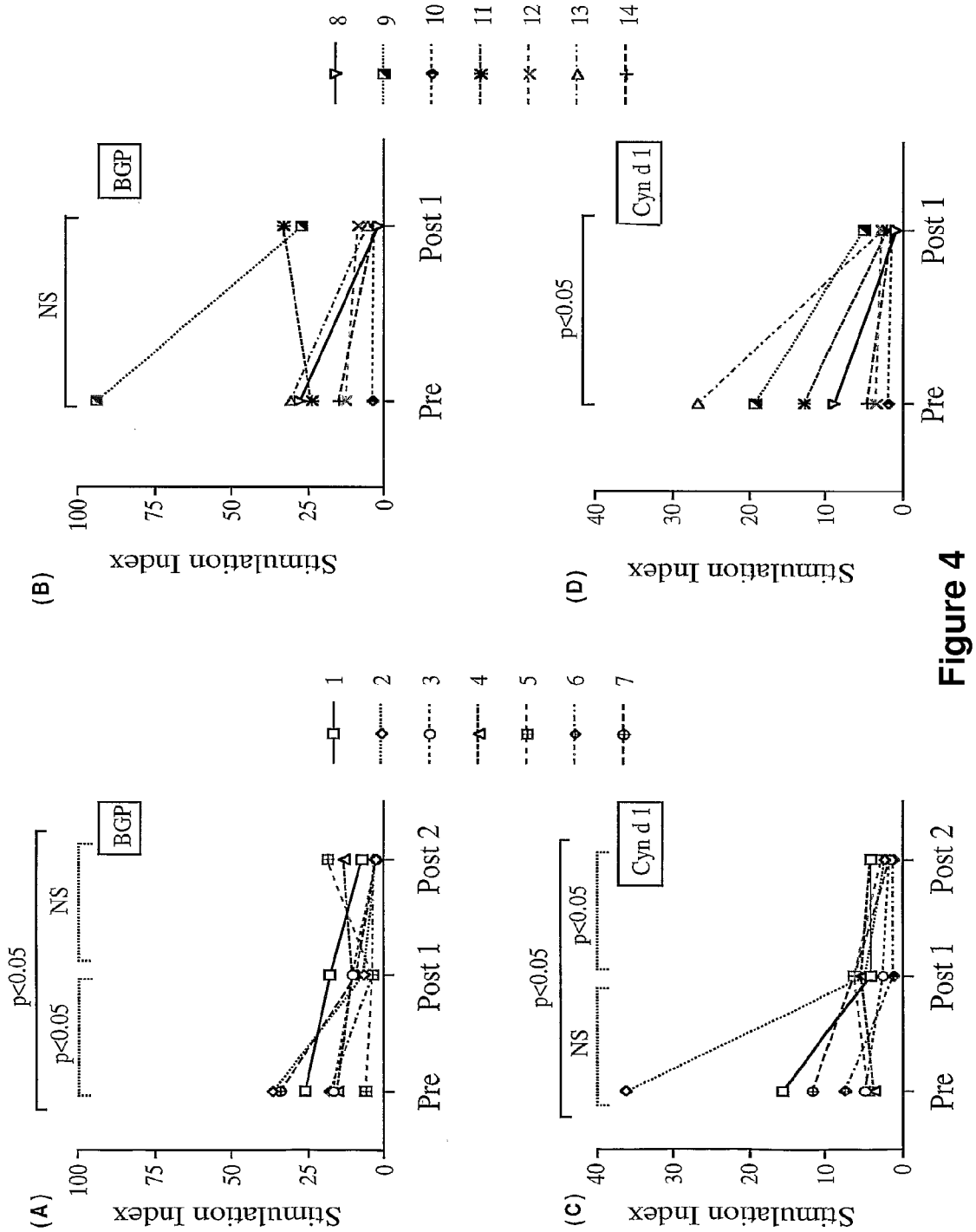

IL-5 and IFN-γ were secreted by the Bermuda grass pollen-specific T cell lines in response to stimulation with Bermuda grass pollen, Cyn d 1 and selected Cyn d 1 peptides that caused T cell proliferation (eg FIG. 3). High levels of both cytokines were produced pre-SIT but post-SIT, there was a marked decrease in IL-5 production in 13/14 patients following their one or two courses of SIT (FIG. 3B and data not shown). IFN-γ levels also decreased post-SIT in 10/14 patients, however, to a lesser extent compared to IL-5 (FIG. 3C and data not shown). IFN-γ secretion was enhanced in 4 patients (8, 9, 11, 13), each of whom had only undertaken one course of SIT when studied. Patient 13 showed increased IL-5 secretion after 1 year of SIT but IFN-γ secretion was enhanced to a greater degree (FIG. 6B, D). After two years of SIT there was negligible secretion of either cytokine by any patient, consistent with the low level of T cell proliferation observed at this time point.

Figure 6:
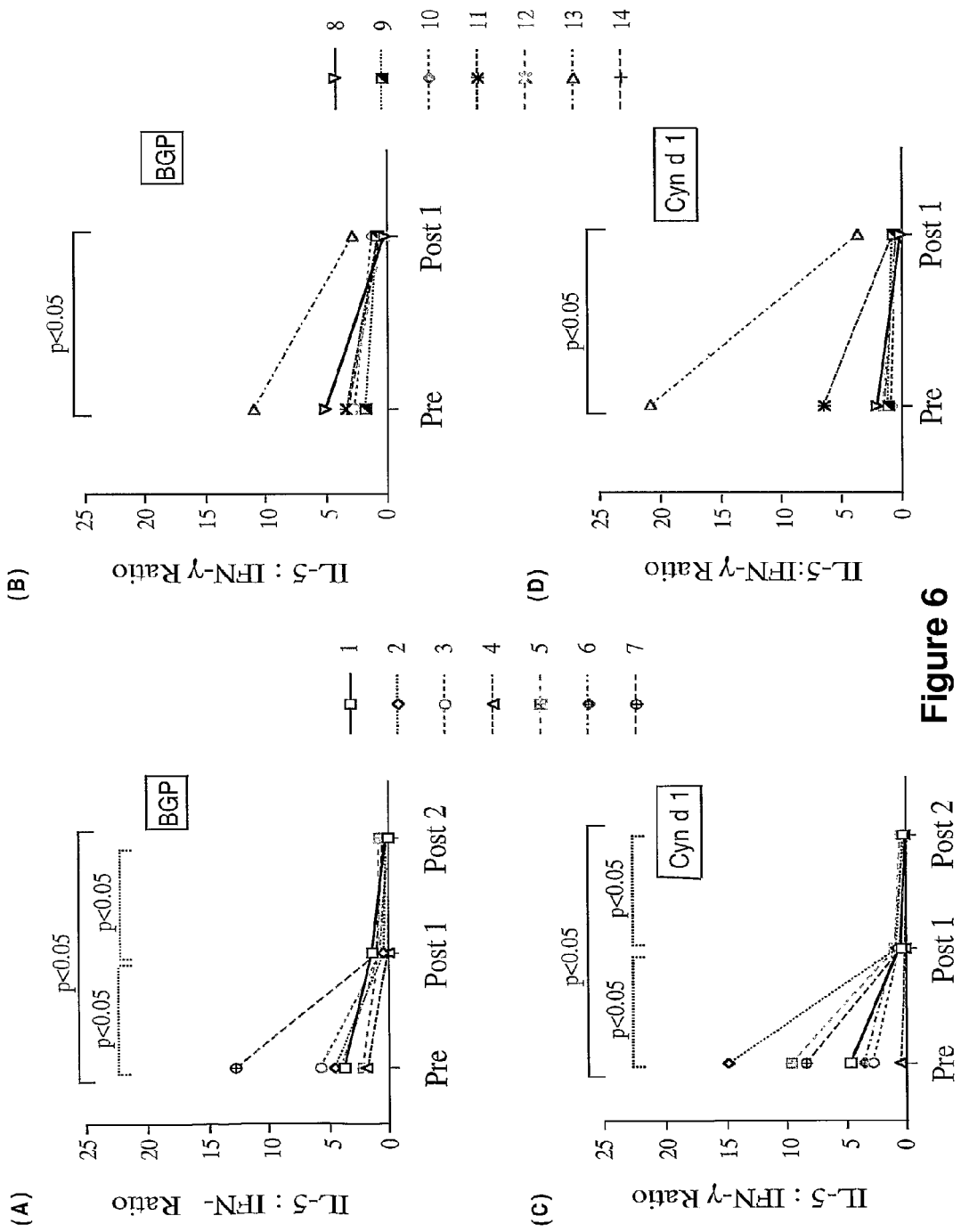

There was a marked shift in the IL-S:IFN-γ ratio during SIT. Using an arbitrary ratio of 1 as a point of comparison, 11/14 patients showed a shift in the IL-S:IFN-γ ratio from $\leq 1$ at 1 year post-SIT for T cells stimulated with both Bermuda grass pollen and Cyn d 1 (FIG. 6). Despite the increased T cell proliferative response observed after stimulation with Bermuda grass pollen following SIT in patients 5 and 11, the IL-S:IFN-γ ratio decreased in both these patients and clinical symptoms also decreased. After two years of SIT, the ratio either remained constant at a low level or continued to decline.

The profile of the IL-5:IFN-γ ratio elicited by peptide stimulation mirrored T cell proliferation (data not shown). After one year of SIT, only seven peptides induced a ration of $\geq 1$ in at least one patient, and after two years of SIT, this was virtually abrogated with only one peptide including a ratio of >1 in two patients.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 3

Clinical characteristics of the Bermuda grass pollen-allergic patients and Bermuda grass pollen-specific IgE before and after one and two (patients 1-7) courses of SIT.

| Patient | Sex | Age | Seasonal Rhinitis | Asthma | Bermuda grass pollen Skin Test Reactivity (mm) | | | Bermuda grass pollen EAST Score (AEU/ml) | | |
|---|---|---|---|---|---|---|---|---|---|---|
| | | | | | Pre-SIT | Post-1 course SIT | Post-2 course SIT | Pre-SIT | Post-1 course SIT | Post-2 course SIT |
| 1 | M | 22 | +++ | ++ | 12 | 10 | 7 | ND | 3 (5.33) | 3 (14.54) |
| 2 | F | 47 | +++ | + | 10 | 8 | 8 | 2 (1.86) | 3 (10.84) | ND |
| 3 | F | 33 | +++ | + | 11 | 11 | 11 | ND | 3 (16.08) | 3 (16.55) |
| 4 | F | 36 | +++ | − | 7 | 4 | 3 | 3 (6.44) | 3 (5.72) | ND |
| 5 | F | 24 | +++ | ++ | 6 | 5 | 8 | 3 (4.84) | 3 (11.83) | ND |
| 6 | F | 45 | +++ | − | 14 | 11 | 11 | 1 (0.45) | 2 (0.87) | 3 (7.12) |
| 7 | F | 30 | +++ | + | ND | ND | 8 | 2 (1.64) | ND | 2 (2.40) |
| 8 | F | 22 | +++ | ++ | 7 | 6 | | 2 (2.70) | 3 (3.823) | |
| 9 | M | 22 | +++ | + | 11 | 5 | | 3 (7.03) | 3 (11.05) | |
| 10 | M | 27 | +++ | − | ND | 13 | | 3 (11.82) | 3 (13.68) | |
| 11 | M | 30 | +++ | ++ | 5 | 11 | | 3 (5.15) | 4 (>17.5) | |
| 12 | F | 47 | +++ | − | 7 | 7 | | 3 (5.29) | 3 (9.28) | |
| 13 | M | 27 | +++ | ++ | 10 | 15 | | 3 (7.06) | ND | |
| 14 | M | 55 | +++ | − | 10 | 5 | | 0 (<0.18) | 2 (0.78) | |

ND = Not done

BIBLIOGRAPHY

Amann et al., 1988, *Gene.,* 69:301-315

Balderi et al., 1987, *Embo J.,* 6:229-234

Blaher B, McCluskey J, Puy R, Czarny D, Rolland J M., *Immunol Cell Biol.,* 1995; 73:17-22

Chang et al., 1999, *Clin Exp Allergy.,* 29:488-496

Creticos P S, Van Metre T E, Mardiney M R., *J Allergy Clin Immunol.,* 73:94-104 (1984)

Djurup R, Malling H, Sondergaard I, Weeke B., *J Allergy Clin Immunol.,* 76:46-55 (1985)

Durham S R, Walker S M, Varga E M, Jacobson M R, O'Brien F, Noble W, Till S J, Hamid Q A., *N Engl J Med.,* 1999; 341:468-475

Ford S A, Baldo B A., *J Allergy Clin Immunol.,* 1987; 79:711-720

Gleich G J, Zimmerman E M, Henderson L L, Yunginger J W., *J Allergy Clin Immunol.,* 70:261-271 (1982)

Jameel et al., 1990, *J. Virol.,* 64:3963-3966

Kimura A, Sasazuki T., Eleventh International Histocompatibility workshop reference protocol for the HLA DNA-typing technique. In: Tsuji K, Aizawa M, Sasazuki, editors. HLA 1991, Proceedings of the 11th International Histocompatibility Workshop and Conference. vol 1. Oxford University Press. 1992

Knapp et al., 1990, *Bio Techniques.,* 8:280-281

Kurjan and Herskowitz., 1982, *Cell.,* 30:933-943

Lichtenstein L M, Ishizaka K, Norman P S, Sobotka A K, Hill B M., *J Clin Invest.,* 52:472-482 (1973)

Li Y, Simons E R, Jay F T, HayGlass K T., *Int Immunol.,* 1996; 8:897-904

Marsh D G, Haddad Z H, Campbell D M., *J Allergy.,* 1970; 46:107-121

Martin B G, Mansfield L E, Nelson H S., *Ann Allergy.,* 1985; 54:99-104

Matthiesen F, Schumacher M J, Løwenstein H., *J Allergy Clin Immunol.,* 1989; 83:1124-1134

O'Hehir R E, Young D B, Kay A B, Lamb J R., *Immunology.,* 62:635-640 (1987)

O'Hehir R E, Askonas B A, Lamb J R., Cell culture: lymphocyte clones. In: Albert W H W, Staines N A, editors. Methods of immunological analysis. Vol 3. Heidelberg: Springer-Verlag; 1993. p 120-138

Orren A, Dowdle E B., *S Afr Med J.,* 1977; 51:586-591

Rolland J, O'Hehir R., *Curr Opin Immunol.,* 1998; 10:640-645

Sambruck et al., 1989, "Molecular Cloning: a laboratory manual, second edition"; Cold Spring Harbour Laboratory Press; Cold Spring Harbour, N.Y.

Schultz et al., 1987, *Gene.,* 54:113-123

Shen H D, Wang S R, Atang R B, Chang Z N, Han S H., *Clin Allergy.,* 1988; 18:401-409

Smith P M, Suphiogl C, Griffith I J, Theriault K, Knox R B, Singh M B., *J Allergy Clin Immunol.,* 1996; 98:331-343

Suphioglu C, Singh M B, Knox R B., *Int Arch Allergy Immunol.,* 1993; 102:144-151

Varney et al., 1990, *British Medical Journal.,* 302:265-269

Varney M D, Tait B D., *Eur. J. Immunogenetics.,* 25:371-374 (1998)

The invention claimed is:

1. An isolated peptide which is in the form of a pharmaceutically acceptable salt thereof, wherein the amino acid sequence of said peptide consists of an amino acid sequence selected from the group consisting of SEQ ID NO: 12, SEQ ID NO: 13, SEQ ID NO: 14, SEQ ID NO: 20, SEQ ID NO: 21, SEQ ID NO: 22, SEQ ID NO: 23, SEQ ID NO: 26 and SEQ ID NO: 27.

2. An isolated peptide which is in the form of a pharmaceutically acceptable salt thereof, wherein the amino acid sequence of said peptide consists of a sequence of at least five contiguous amino acids from an amino acid sequence selected from the group consisting of SEQ ID NO:14, SEQ ID NO: 22 and SEQ ID NO: 23.

3. The peptide according to claim 1, consisting of an amino acid sequence selected from the group consisting of SEQ ID NO: 14, SEQ ID NO: 22; SEQ ID NO: 23, SEQ ID NO: 26 and SEQ ID NO: 27.

4. The peptide according to claim 1, consisting of SEQ ID NO: 14.

5. The peptide according to claim 1, consisting of SEQ ID NO: 22.

6. The peptide according to claim 1, consisting of SEQ ID NO: 23.

7. A method for decreasing sensitivity to Bermuda Grass pollen in a subject with, or at risk of Bermuda Grass pollen hypersensitivity in a subject, which condition is characterized by an aberrant, unwanted or otherwise inappropriate immune response to Cyn d I, said method comprising administering to said subject an effective amount of a peptide which is in the form of a pharmaceutically acceptable salt thereof according to claim 2.

8. The method of claim 7, which comprises administering to said subject an effective amount of a peptide consisting of SEQ ID NO: 14.

9. The method of claim 7, which comprises administering to said subject an effective amount of a peptide consisting of SEQ ID NO: 22.

10. The method of claim 7, which comprises administering to said subject an effective amount of a peptide consisting of SEQ ID NO: 23.

11. A sterile injectable pharmaceutical composition comprising at least one peptide of claim 1 or 2 and a pharmaceutically acceptable carrier.

12. A sterile injectable pharmaceutical composition according to claim 11, wherein said salt is an acid addition salt.

13. A sterile injectable pharmaceutical composition according to claim 11, wherein said salt is hydrochloride, hydrobromide, sulphate, phosphate, maleate, acetate, benzoate, succinate, malate, ascorbate or tartrate.

14. A sterile injectable pharmaceutical composition according to claim 11, wherein said salt is hydrochloride or acetate.

15. An isolated peptide of claim 1 or 2, wherein said salt is an acid addition salt.

16. An isolated peptide of claim 1 or 2, wherein said salt is hydrochloride, hydrobromide, sulphate, phosphate, maleate, acetate, benzoate, succinate, malate, ascorbate or tartrate.

17. An isolated peptide of claim 1 or 2, wherein said salt is hydrochloride or acetate.

* * * * *